(12) United States Patent
Galvin et al.

(10) Patent No.: US 9,026,147 B2
(45) Date of Patent: May 5, 2015

(54) DEFIBRILLATOR LOCATION TRACKING DEVICE

(71) Applicant: Physio-Control, Inc., Redmond, WA (US)

(72) Inventors: Moira Montgomery Galvin, Kirkland, WA (US); Kevin C Drew, Snohomish, WA (US); Todd Klump, Kirland, WA (US); John Robert Knapinski, Kirkland, WA (US); Dana S Lewis, Woodinville, WA (US); Steve M Silkes, Woodinville, WA (US)

(73) Assignee: Physio-Control, Inc., Redmond, WA (US)

( * ) Notice: Subject to any disclaimer, the term of this patent is extended or adjusted under 35 U.S.C. 154(b) by 72 days.

(21) Appl. No.: 13/779,772

(22) Filed: Feb. 28, 2013

(65) Prior Publication Data

US 2014/0087762 A1     Mar. 27, 2014

Related U.S. Application Data

(60) Provisional application No. 61/704,975, filed on Sep. 24, 2012.

(51) Int. Cl.
*H04W 4/04* (2009.01)
*G01S 19/17* (2010.01)
(Continued)

(52) U.S. Cl.
CPC ................ *H04W 4/04* (2013.01); *H04W 4/043* (2013.01); *H04L 67/12* (2013.01); *G01S 19/17* (2013.01); *G01S 5/0226* (2013.01); *G06F 19/3418* (2013.01)

(58) Field of Classification Search
CPC ...... H04W 64/00; H04W 4/02; G08B 25/016; A61B 5/0002; G06Q 10/08
USPC .......... 455/456.1–3; 340/539.11–13; 607/2–9
See application file for complete search history.

(56) References Cited

U.S. PATENT DOCUMENTS 6,370,428 B1    4/2002   Snyder et al.
7,006,865 B1    2/2006   Cohen et al.
(Continued)

FOREIGN PATENT DOCUMENTS

EP          0801959 A2    10/1997
EP          0923961 A1    6/1999
WO          13056194 A1   4/2013

OTHER PUBLICATIONS

Int'l Search Report and Written Opinion, PCT/US2012/071436, mailed Apr. 10, 2013, 13 pages.
(Continued)

*Primary Examiner* — Cong Tran
(74) *Attorney, Agent, or Firm* — The Juhasz Law Firm

(57) ABSTRACT

A defibrillator is disclosed for communication with a transmitter associated with a location. The defibrillator is configured to generate an electronic signature for determining a position of the defibrillator within the location. The electronic signature includes electronic data correlating the position of the defibrillator to the transmitter. The electronic data may include GPS data. The defibrillator is configured to generate the electronic signature during a first and a second window of time to define a first and a second electronic signature. A differential between the first and the second electronic signatures corresponds to a positional state of the defibrillator, indicating movement within or between two locations. In a disclosed system, the first electronic signature is stored in a database and a server is configured to generate the differential and to communicate the positional state of the defibrillator to a stakeholder. Methods of use are also disclosed.

36 Claims, 13 Drawing Sheets

(51) Int. Cl.
*G01S 5/02* (2010.01)
*G06F 19/00* (2011.01)
*H04L 29/08* (2006.01)

(56) References Cited

U.S. PATENT DOCUMENTS

| | | | |
|---|---|---|---|
| 7,277,752 B2 * | 10/2007 | Matos | 607/5 |
| 7,565,197 B2 * | 7/2009 | Haubrich et al. | 607/30 |
| 7,787,946 B2 * | 8/2010 | Stahmann et al. | 607/3 |
| 8,040,246 B2 | 10/2011 | Graves et al. | |
| 8,054,177 B2 | 11/2011 | Graves et al. | |
| 8,154,246 B1 | 4/2012 | Heitmann | |
| 8,694,100 B2 * | 4/2014 | Drew et al. | 607/31 |
| 2001/0041920 A1 | 11/2001 | Starkweather et al. | |
| 2003/0097160 A1 | 5/2003 | Caby et al. | |
| 2003/0167074 A1 | 9/2003 | Merry | |
| 2004/0027244 A9 * | 2/2004 | Menard | 340/573.1 |
| 2006/0149321 A1 | 7/2006 | Merry et al. | |
| 2006/0149323 A1 | 7/2006 | Merry et al. | |
| 2006/0173498 A1 | 8/2006 | Banville | |
| 2008/0129465 A1 * | 6/2008 | Rao | 340/286.02 |
| 2008/0167054 A1 * | 7/2008 | Shaheen | 455/458 |
| 2009/0264948 A1 | 10/2009 | Tamura et al. | |
| 2009/0295326 A1 | 12/2009 | Daynes et al. | |
| 2010/0070772 A1 * | 3/2010 | Nakamura et al. | 713/176 |
| 2010/0114236 A1 | 5/2010 | Jiang et al. | |
| 2011/0208259 A1 | 8/2011 | Pearce et al. | |
| 2011/0295078 A1 | 12/2011 | Reid et al. | |
| 2012/0191476 A1 * | 7/2012 | Reid et al. | 705/3 |
| 2013/0063550 A1 * | 3/2013 | Ritchey et al. | 348/36 |
| 2013/0096649 A1 | 4/2013 | Martin et al. | |
| 2013/0142367 A1 * | 6/2013 | Berry et al. | 381/315 |
| 2014/0236615 A1 * | 8/2014 | Ragusky et al. | 705/2 |

OTHER PUBLICATIONS

Int'l Search Report and Written Opinion, PCT/US2012/071461, mailed Apr. 10, 2013, 14 pages.
ISR and Written Opinion, PCT/US12/71450, issued May 24, 2013 (10 pages).
Int'l Search Report and Written Opinion, PCT/US2012/071488, mailed Feb. 8, 2013, 11 pages.

\* cited by examiner

DEFIBRILLATION SCENE

| TYPE OF EXTERNAL DEFIBRILLATOR | INTENDED TO BE USED BY PERSONS: | |
|---|---|---|
| | IN THE MEDICAL PROFESSIONS | NOT IN THE MEDICAL PROFESSIONS |
| DEFIBRILLATOR – MONITOR | √ | |
| AED | √ | √ |

TWO MAIN TYPES OF
EXTERNAL DEFIBRILLATORS

COMPONENTS OF EXTERNAL DEFIBRILLATOR

DEFIBRILLATOR LOCATION TRACKING DEVICE

FIELD

This invention generally relates to external defibrillators.

BACKGROUND

In humans, the heart beats to sustain life. In normal operation, it pumps blood through the various parts of the body. More particularly, the various chamber of the heart contract and expand in a periodic and coordinated fashion, which causes the blood to be pumped regularly. More specifically, the right atrium sends deoxygenated blood into the right ventricle. The right ventricle pumps the blood to the lungs, where it becomes oxygenated, and from where it returns to the left atrium. The left atrium pumps the oxygenated blood to the left ventricle. The left ventricle, then, expels the blood, forcing it to circulate to the various parts of the body and from where it returns to the right atrium to start the oxygenation-deoxygenation cycle of the blood all over again.

The heart chambers pump because of the heart's electrical control system. More particularly, the sinoatrial (SA) node generates an electrical impulse, which generates further electrical signals. These further signals cause the above-described contractions of the various chambers in the heart to occur in the correct sequence. The electrical pattern created by the sinoatrial (SA) node is called a sinus rhythm.

Sometimes, however, the electrical control system of the heart malfunctions, which can cause the heart to beat irregularly, or not at all. The cardiac rhythm is then generally called an arrhythmia. Arrhythmias may be caused by electrical activity from locations in the heart other than the SA node. Some types of arrhythmia may result in inadequate blood flow, thus reducing the amount of blood pumped to the various parts of the body. Some arrhythmias may even result in a Sudden Cardiac Arrest (SCA). In an SCA, the heart fails to pump blood effectively, and, if not corrected, can result in death. It is estimated that SCA results in more than 250,000 deaths per year in the United States alone. Further, an SCA may result from a condition other than an arrhythmia.

One type of arrhythmia associated with SCA is known as Ventricular Fibrillation (VF). VF is a type of malfunction where the ventricles make rapid, uncoordinated movements, instead of the normal contractions. When that happens, the heart does not pump enough blood to deliver enough oxygen to the vital organs. The person's condition will deteriorate rapidly and, if not corrected in time, will result in death, e.g. within ten minutes.

Ventricular Fibrillation can often be reversed using a life-saving device called a defibrillator. A defibrillator, if applied properly, can administer an electrical shock to the heart. The shock may terminate the VF, thus giving the heart the opportunity to resume normal contractions in pumping blood. If VF is not terminated, the shock may be repeated, often at escalating energies.

A challenge with defibrillation is that the electrical shock must be administered very soon after the onset of VF. There is not much time to do this since the survival rate of persons suffering from VF decreases by about 10% for each minute the administration of a defibrillation shock is delayed. After about 10 minutes the rate of survival for SCA victims averages less than 2%.

The challenge of defibrillating early after the onset of VF is being met in a number of ways. First, for some people who are considered to be at a higher risk of VF or other heart arrythmias, an Implantable Cardioverter Defibrillator (ICD) can be implanted surgically. An ICD can monitor the person's heart, and administer an electrical shock as needed. As such, an ICD reduces the need to have the higher-risk person be monitored constantly by medical personnel.

Regardless, VF can occur unpredictably, even to a person who is not considered at risk. As such, VF can be experienced by many people who lack the benefit of ICD therapy. When VF occurs to a person who does not have an ICD, they collapse, because the blood flow has stopped. They should receive therapy quickly after the onset of VF or they will die.

For a VF victim without an ICD, a different type of defibrillator can be used, which is called an external defibrillator. External defibrillators have been made portable, so they can be brought to a potential VF victim quickly enough to revive them.

During VF, the person's condition deteriorates because the blood is not flowing to the brain, heart, lungs, and other organs. The blood flow must be restored, if resuscitation attempts are to be successful.

Cardiopulmonary Resuscitation (CPR) is one method of forcing blood to again flow in a person experiencing cardiac arrest. In addition, CPR is the primary recommended treatment for some patients with some kinds of non-VF cardiac arrest, such as asystole and pulseless electrical activity (PEA). CPR is a combination of techniques that include chest compressions to force blood circulation, and rescue breathing to force respiration.

Properly administered CPR provides oxygenated blood to critical organs of a person in cardiac arrest, thereby minimizing the deterioration that would otherwise occur. As such, CPR can be beneficial for persons experiencing VF, because it slows down the deterioration that would otherwise occur while a defibrillator is being retrieved. For patients with an extended down-time, survival rates are higher if CPR is administered prior to defibrillation.

Defibrillators are thus seen to provide a valuable asset for use in patient health care. A system that enhances the value of these assets to defibrillator operators and stakeholders enhances the effectiveness of the defibrillation process. While some advanced systems provide defibrillator asset management for this purpose, defibrillator operators and stakeholders may benefit from additional defibrillator management.

BRIEF SUMMARY

The present description gives instances of devices, systems, software and methods, the use of which may help overcome problems and limitations of the prior art.

A defibrillator is disclosed for communication with a transmitter associated with a location. The defibrillator is configured to generate an electronic signature for determining a position of the defibrillator within the location. The electronic signature includes electronic data correlating the position of the defibrillator to the transmitter. The defibrillator is configured to generate the electronic signature during a first window of time to define a first electronic signature and to generate the electronic signature during a second window of time to define a second electronic signature. A differential between the first and the second electronic signatures corresponds to a positional state of the defibrillator, indicating movement within or between two locations.

An illustrative system for determining the positional state of a defibrillator includes a transmitter, a defibrillator, and a server. The transmitter is associated with a location and the defibrillator is in communication with the transmitter. The defibrillator is configured to generate an electronic signature for determining a position of the defibrillator within the location. The electronic signature includes electronic data correlating the position of the defibrillator to the transmitter. The defibrillator is configured to generate the electronic signature during a first window of time to define a first electronic signature and to generate the electronic signature during a second window of time to define a second electronic signature. The server is in communication with the transmitter and is configured to determine the differential between the first electronic signature and the second electronic signature and the positional state of the defibrillator. A differential between the first and the second electronic signatures corresponds to a positional state of the defibrillator, indicating movement within or between two locations.

In an illustrative method for determining the positional state of a defibrillator, an electronic signature for a defibrillator is generated for determining a position of the defibrillator within a location. The electronic signature includes electronic data correlating the position of the defibrillator to a transmitter. The electronic signature is generated during a first window of time to define a first electronic signature and during a second window of time to define a second electronic signature. The difference between the first electronic signature and the second electronic signature is determined. A differential between the first and the second electronic signatures corresponds to a positional state of the defibrillator, indicating movement within or between two locations.

In an alternative embodiment, a defibrillator is disclosed for communication with a transmitter associated with a location. The defibrillator may be configured to generate an electronic signature for determining a position of the defibrillator within the location. The electronic signature may include electronic data correlating the position of the defibrillator to the transmitter. The electronic data correlating the position of the defibrillator to the transmitter may include GPS data.

These and other features and advantages of this description will become more readily apparent from the following Detailed Description, which proceeds with reference to the drawings, in which:

BRIEF DESCRIPTION OF THE DRAWINGS

FIG. 1 is an illustrative diagram of a scene showing the use of an external defibrillator to save the life of a person according to this disclosure.

FIG. 2 is a table listing two illustrative types of the external defibrillator shown in FIG. 1, and who they might be used by.

DETAILED DESCRIPTION

Broadly speaking, a defibrillator is disclosed for communication with a transmitter associated with a location. The defibrillator is configured to generate an electronic signature for determining a position of the defibrillator within the location. The electronic signature includes electronic data correlating the position of the defibrillator to the transmitter. The defibrillator is configured to generate the electronic signature during a first and a second window of time to define a first and a second electronic signature. A differential between the first and the second electronic signatures corresponds to a positional state of the defibrillator, indicating movement within or between two locations. The electronic data correlating the position of the defibrillator to the transmitter may include GPS data. In a disclosed system, the first electronic signature is stored in a database and a server is configured to generate the differential and to communicate the positional state of the defibrillator to a stakeholder. Methods of use are also disclosed.

A comprehensive understanding of the foregoing and other aspects of this disclosure begins with the following description on the operation of defibrillators.

Figures 1, 2:
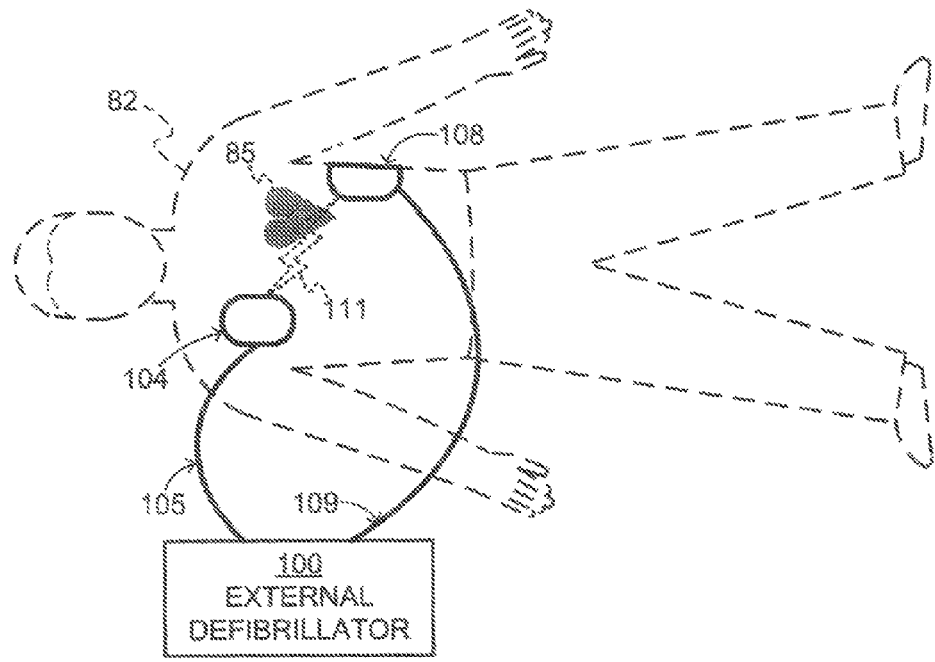

FIG. 1 is a diagram of a defibrillation scene showing the use of an external defibrillator to save the life of a person according to this disclosure. As shown, a person 82 is lying on his back. Person 82 could be a patient in a hospital, or someone found unconscious, and then turned over onto his back. Person 82 is experiencing a condition in their heart 85, which could be Ventricular Fibrillation (VF).

A portable external defibrillator 100 has been brought close to person 82. At least two defibrillation electrodes 104, 108 are typically provided with external defibrillator 100, and are sometimes called electrodes 104, 108. Electrodes 104, 108 are coupled together with external defibrillator 100 via respective electrode leads 105, 109. A rescuer (not shown) has attached electrodes 104, 108 to the skin of person 82. Defibrillator 100 is administering, via electrodes 104, 108, a brief, strong electric pulse 111 through the body of person 82. Pulse 111, also known as a defibrillation shock, also goes through heart 85, in an attempt to restart it, for saving the life of person 82.

Defibrillator 100 can be one of different types, each with different sets of features and capabilities. The set of capabilities of defibrillator 100 is determined based upon who would use it and what training they would be likely to have. Examples are now described.

FIG. 2 is a table listing two typical types of external defibrillators, and who they are primarily intended to be used by. A first type of defibrillator 100 is generally called a defibrillator-monitor, because the defibrillator part is typically formed as a single unit with a patient monitor part. A defibrillator-monitor is sometimes called monitor-defibrillator. A defibrillator-monitor is intended to be used by persons in the medical profession, such as doctors, nurses, paramedics, emergency medical technicians, etc. who may be trained to provide medical treatment to the patient during a defibrillation process based upon information provided by the monitor. Such a defibrillator-monitor is intended to be used in a pre-hospital or hospital scenario.

The defibrillator part may be dedicated to a particular mode of operation. Alternatively, the defibrillator part may be configured to operate in more than one modes of operation. One mode of operation of the defibrillator part may be that of an automated defibrillator, which can determine whether a shock is needed and, if so, charge to a predetermined energy level and instruct the user to administer the shock. Another mode of operation may be that of a manual defibrillator, where the user determines the need and controls administering the shock. In this embodiment, one illustrative defibrillator is configured to enable both automated defibrillation and manual defibrillation modes of operation depending upon the selection of the user. As a patient monitor, the device has features additional to what is minimally needed for mere operation as a defibrillator. These features can be for monitoring physiological indicators of a person in an emergency scenario. These physiological indicators are typically monitored as signals. For example, these signals can include a person's full ECG (electrocardiogram) signals, or impedance between two electrodes. Additionally, these signals can be about the person's temperature, non-invasive blood pressure (NIBP), arterial oxygen saturation/pulse oximetry (SpO2), the concentration or partial pressure of carbon dioxide in the respiratory gases, which is also known as capnography, and so on. These signals can be further stored and/or transmitted as patient data.

A second type of external defibrillator 100 is generally called an AED, which stands for "Automated External Defibrillator". An AED typically makes the shock/no shock determination by itself, automatically. Indeed, it can sense enough physiological conditions of the person 82 via only the shown defibrillation electrodes 104, 108 of FIG. 1. In its present embodiments, an AED can either administer the shock automatically, or instruct the user to do so, e.g. by pushing a button. Being of a much simpler construction, an AED typically costs much less than a defibrillator-monitor. As such, it makes sense for a hospital, for example, to deploy AEDs at its various floors, in case the more expensive defibrillator-monitor is more critically being deployed at an Intensive Care Unit, and so on.

AEDs, however, can also be used by people who are not trained in the medical profession. More particularly, an AED can be used by many professional first responders, such as policemen, firemen, etc. Even a person with only first-aid training can use one. And AEDs increasingly can supply instructions to whoever is using them.

AEDs are thus particularly useful, because it is so critical to respond quickly, when a person suffers from VF. Often, the people who will first reach the VF sufferer may not be in the medical profession.

Increasing awareness of the short survival time of a patient experiencing a VF, has resulted in AEDs being deployed more pervasively in public or semi-public spaces, enabling members of the public to use one provided they have obtained first aid and CPR/AED training. In this way, defibrillation can be administered sooner after the onset of VF, to hopefully be effective in rescuing the person.

There are additional types of external defibrillators, which are not listed in FIG. 2. For example, a hybrid defibrillator can have aspects of an AED, and also of a defibrillator-monitor. An illustrative example may be an AED provided with an ECG monitoring capability.

Figure 3:
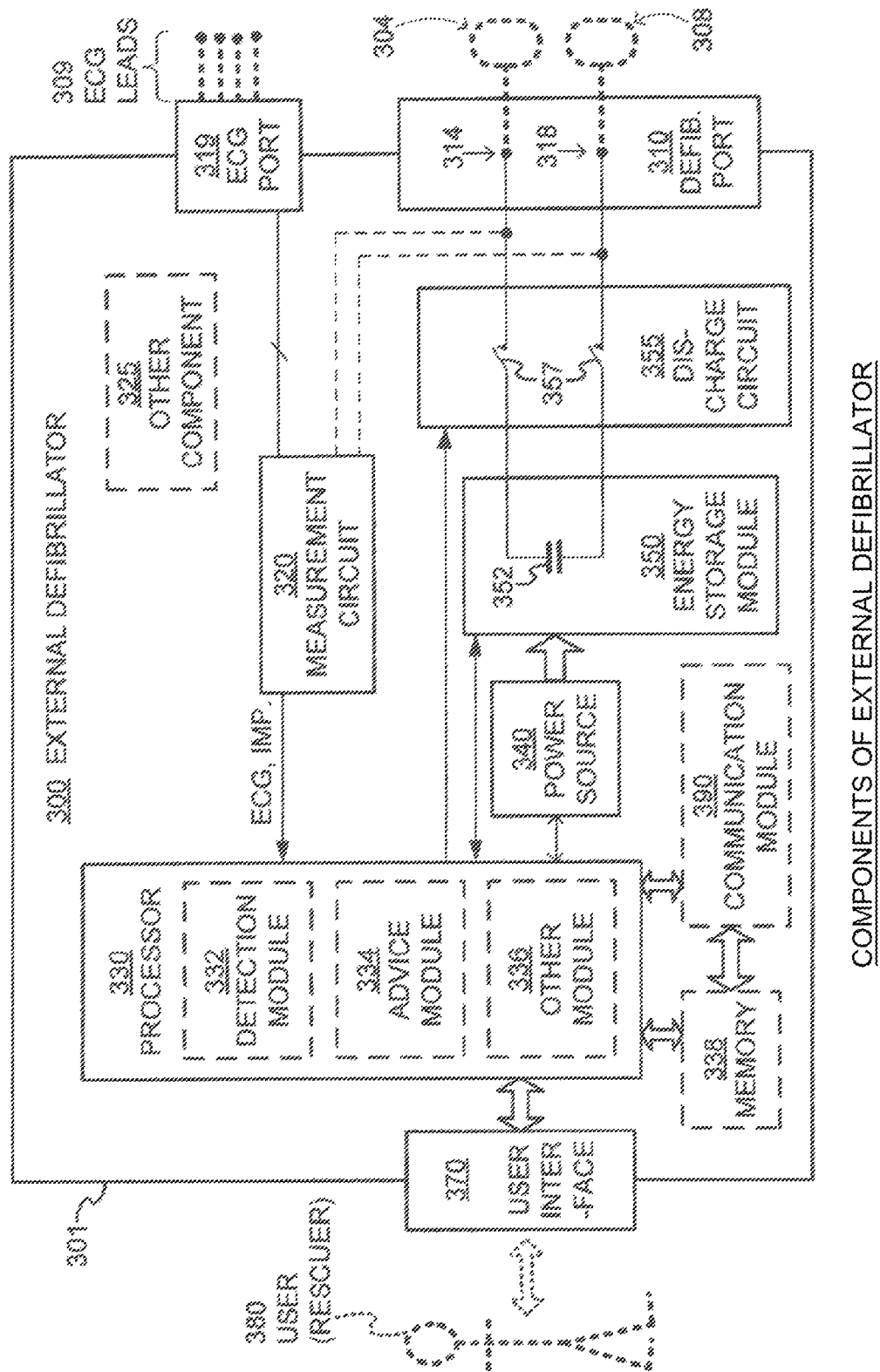
FIG. 3 is a diagram showing components of an external defibrillator, such as the one shown in FIG. 1, configured in an illustrative embodiment according to this disclosure.

FIG. 3 is a diagram showing components of an external defibrillator 300 configured in an illustrative embodiment according to this disclosure. These components can be configured, for example, in external defibrillator 100 of FIG. 1. Plus, these components of FIG. 3 can be provided in a housing 301, which is also known as casing 301.

External defibrillator 300 is intended for use by a user 380, who would be the rescuer. Defibrillator 300 typically includes a defibrillation port 310, which may be configured as a socket (not shown) in housing 301. Defibrillation port 310 includes nodes 314, 318. Defibrillation electrodes 304, 308, which can be similar to electrodes 104, 108 in FIG. 1, can be plugged into defibrillation port 310, so as to make electrical contact with nodes 314, 318, respectively. It is also possible that electrodes can be hard-wired to defibrillation port 310, etc. Either way, defibrillation port 310 can be used for guiding to person 82 via electrodes an electrical charge that has been stored in defibrillator 300, as discussed below.

If defibrillator 300 is actually a defibrillator-monitor, as was described with reference to FIG. 2, then it will typically also have an ECG port 319 in housing 301, for plugging in ECG leads 309. ECG leads 309 can help sense an ECG signal, e.g. a 12-lead signal, or a signal taken from a different number of leads. Moreover, a defibrillator-monitor could have additional ports (not shown), and another component 325 for the above described additional features, such as for receipt of patient signals.

Defibrillator 300 also includes a measurement circuit 320. Measurement circuit 320 receives physiological signals from ECG port 319, and also from other ports, if provided. These physiological signals are sensed, and information about them is rendered by circuit 320 as data, or other signals, etc.

If defibrillator 300 is actually an AED, it may lack ECG port 319. Measurement circuit 320 can obtain physiological signals in this case through nodes 314, 318 instead, when defibrillation electrodes 304, 308 are attached to person 82. In these cases, a person's ECG signal can be sensed as a voltage difference between electrodes 304, 308. Plus, impedance between electrodes 304, 308 can be sensed for detecting, among other things, whether these electrodes 304, 308 have been inadvertently disconnected from the person.

Defibrillator 300 also includes a processor 330. Processor 330 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 may include a number of modules. One such module can be a detection module 332, which senses outputs of measurement circuit 320. Detection module 332 can include a VF detector. Thus, the person's sensed ECG can be used to determine whether the person is experiencing VF.

Another such module in processor 330 can be an advice module 334, which arrives at a piece of instructional advice based on outputs of detection module 332. Advice module 334 can include a Shock Advisory Algorithm residing in a memory unit (not shown) in the advice module for instructing the processor to implement decision rules, etc. Alternatively, the Shock Advisory Algorithm may reside in part or in whole on a memory 338 of the defibrillator. The instruction to the processor can be to shock, to not shock, to administer other forms of therapy, and so on. If the instruction to the processor is to shock, in some external defibrillator embodiments, the processor is configured to report that instruction to the user via user interface 370, and to prompt the user to do it. In other embodiments, the processor may be configured to execute the instructional advice, by administering the shock. If the instructional advice is to administer CPR, the processor may be configured to enable defibrillator 300 to issue prompts to administer CPR, etc.

Processor 330 can include additional modules, such as module 336, for other functions. In addition, if other component 325 is provided, it may be operated in part by processor 330 or by another processor.

Defibrillator 300 optionally further includes the memory 338, which can work together with processor 330. Memory 338 may be implemented in any number of ways. Such ways include, by way of example and not of limitation, nonvolatile memories (NVM), read-only memories (ROM), random access memories (RAM), any combination of these, etc. Memory 338, if provided, may include programs containing instructions for execution by processor 330 or other processors that may be included in the external defibrillator. The programs provide instructions for execution by the processor 330, and can also include instructions regarding protocols and decision making analytics, etc. that can be used by advice module 334. In addition, memory 338 can store prompts for user 380, etc. Moreover, memory 338 can store patient data.

Defibrillator 300 may also include a power source 340. To enable portability of defibrillator 300, power source 340 typically includes a battery. Such a battery is typically implemented as a battery pack, which can be rechargeable or not. Sometimes, a combination is used, of rechargeable and non-rechargeable battery packs. Other embodiments of power source 340 can include an AC power override, whereby AC power, instead of power from power source 340 is delivered to an energy storage module 350 when AC power is available. In some embodiments, power source 340 is controlled by processor 330.

Defibrillator 300 additionally includes the energy storage module 350. Module 350 is where electrical energy is stored in preparation for a sudden discharge to administer a shock. The charge to module 350 from power source 340 to the right amount of energy can be controlled by processor 330. In typical implementations, module 350 includes one or more capacitors 352, and may include other circuitry.

Defibrillator 300 moreover includes a discharge circuit 355. Circuit 355 can be controlled to permit the energy stored in module 350 to be discharged to nodes 314, 318, and thus also to defibrillation electrodes 304, 308. Circuit 355 can include one or more switches 357. Those can be made in a number of ways, such as by an H-bridge, and in other ways well known in the art.

Defibrillator 300 further includes the user interface 370 for user 380. User interface 370 can be made in any number of ways. For example, interface 370 may include a screen, to display a parameter of a patient that is detected and measured, provide visual feedback to the rescuer for their resuscitation attempts, and so on. Interface 370 may also include a speaker, to issue voice prompts, etc. Interface 370 may additionally include various controls, such as pushbuttons, keyboards, and so on. In addition, discharge circuit 355 can be controlled by processor 330, or directly by user 380 via user interface 370, and so on.

Defibrillator 300 can optionally include other components. For example, a communication module 390 may be provided for communicating with other devices. Such communication can be performed wirelessly, or via wire, or by infrared communication, and so on. In this way, data can be communicated from the defibrillator 300 to external devices, such as patient data, incident information, therapy attempted, CPR performance, and so on.

Having thus introduced background on the general operation of a defibrillator, we now turn to features that are provided by this disclosure.

Briefly stated, a defibrillator is disclosed for communication with a transmitter associated with a location. The defibrillator is configured to generate an electronic signature for determining a position of the defibrillator within the location. The electronic signature includes electronic data correlating the position of the defibrillator to the transmitter. The electronic data correlating the position of the defibrillator to the transmitter may include GPS data. The defibrillator is configured to generate the electronic signature during a first and a second window of time to define a first and a second electronic signature. A differential between the first and the second electronic signatures corresponds to a positional state of the defibrillator, indicating movement within or between two locations. In an illustrative disclosed system, the first electronic signature is stored in a database and a server is configured to generate the differential and to communicate the positional state of the defibrillator to a stakeholder. Methods of use are also disclosed.

Figure 4:
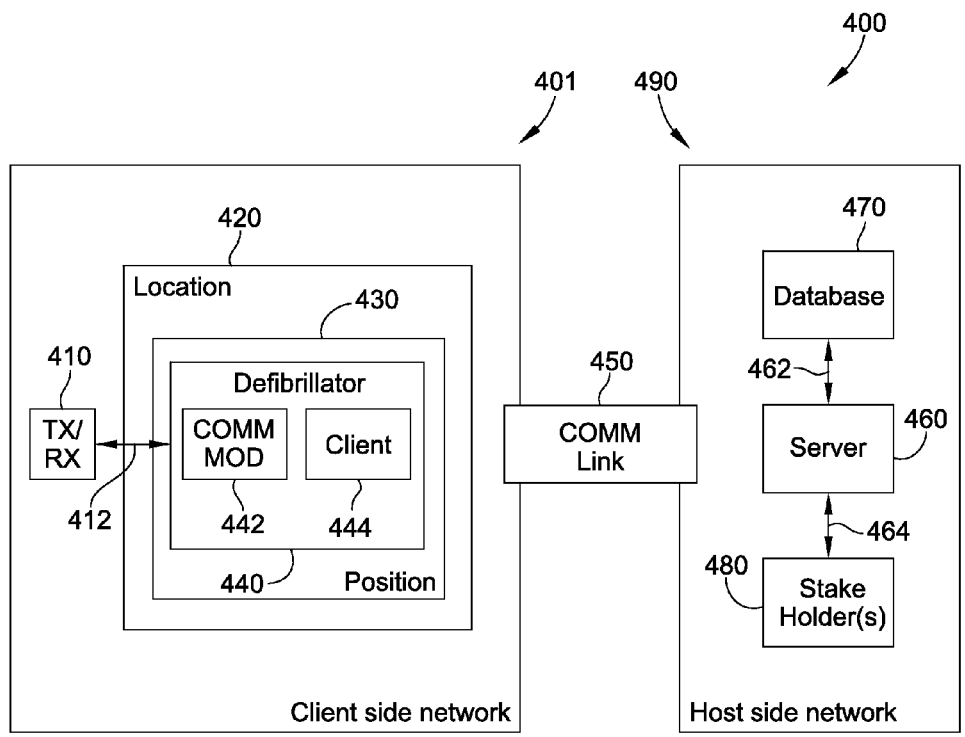
FIG. 4 illustrates a location tracking system according to this disclosure.

FIG. 4 illustrates a location tracking system 400 according to this disclosure. Location tracking system 400 comprises a defibrillator 440 in a client side network 401, a server 460, a database 470, and one or more stake holders 480 in a host side network 490, and a communication link 450 configured to connect the defibrillator to the server. The network 401 includes a transmitter/receiver 410 (otherwise referred to herein as TX/RX 410). The defibrillator occupies a position 430 within a location 420 within the client side network 401.

The term position 430, as used herein, means a place where the defibrillator 440 has been put. It is the particular space that is occupied by the defibrillator at a specific point in time. The term location 420 as used herein means a particular geographical topography within the client side network 401. The particular geographical topography may be the floor plan of a single or multi-level building, a hospital, a section of a building or hospital, a room in a building or hospital, an airport, a mall, an office building or an office within a building. It may also be the floor plan of an emergency vehicle like an ambulance vehicle or a fire truck. The location may reside in any public or private or other space. By the term topography is meant any attribute of a location such as the area defined by a location, the height of a location, one or more volumes of space defined by that location, a floor plan of a location, or any other topographical depiction of a location.

Figure 5:
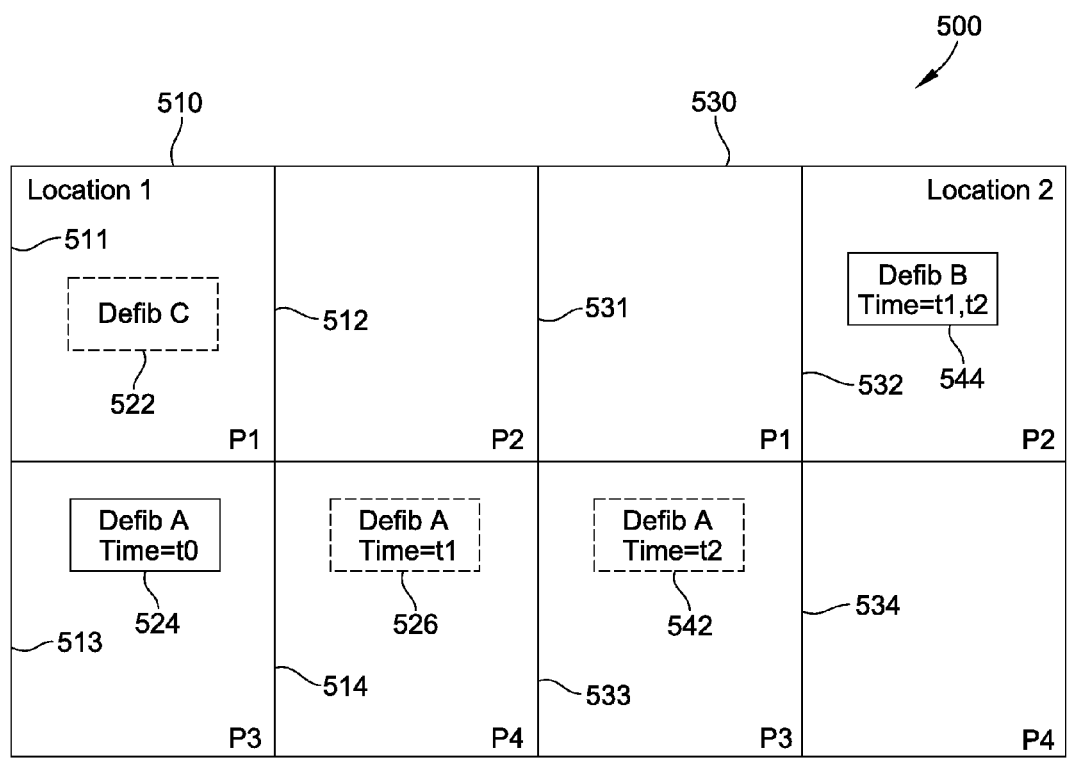
FIG. 5 shows an embodiment of a depiction of predetermined positions in two locations in a network according to an illustrative embodiment of this disclosure.

FIG. 5 shows an embodiment of a depiction of predetermined positions residing within two locations in a network according to an illustrative embodiment of this disclosure. The embodiment depicts a footprint 500 including a first location LOCATION 1 510 and a second location LOCATION 2 530. LOCATION 1 510 includes four positions denoted by P1, P2, P3, and P4 bearing numbers 511-514, respectively. LOCATION 2 530 includes four positions denoted by P1, P2, P3, and P4 bearing numbers 531-534, respectively. FIG. 5 also shows three defibrillators DEFIB A 524, DEFIB B 544, and DEFIB C 522 within the footprint 500 defined by LOCATION 1 and LOCATION 2 together. DEFIB A 524 and DEFIB B 544 shown in solid lines illustrate that these two defibrillators occupy the positions P3 513 of LOCATION 1 510 and P2 532 of LOCATION 2 530 in the present time. DEFIB A 524 is also shown in phantom lines as DEFIB A 526 occupying position 514 of LOCATION 1 510 and as DEFIB A 542 occupying position 533 of LOCATION 2 530, respectively, at times t1 and t2, respectively; thereby illustrating the positions that DEFIB A has taken at times t1 and t2 with respect to the position taken by DEFIB A at time t0.

In other words, together with the solid lines depicting DEFIB A at time t0, the phantom lines of DEFIB A 526 at time t1 shows the movement of DEFIB A within LOCATION 1 510 from position 513 to position 514; thereby showing the movement of DEFIB A between two positions within a single location over a first period or window of time. This may occur, for example, when DEFIB A is moved between two places within a building. In addition, together with the phantom lines of DEFIB A 526, the phantom lines of DEFIB A 542 shows the movement of DEFIB A from within LOCATION 1 510 at position 514 to position 533 within a different location, namely, LOCATION 2 530; thereby showing the movement of DEFIB A between two locations over a second period or window of time. This may occur, for example, when DEFIB A is moved from a place within a first building to a place within a second building. The phantom line of DEFIB C 522 illustrates that DEFIB C 522 is not located in LOCATION 1 510 at the present time but occupies position P1 511 at a future point in time. In other words, DEFIB C is not within footprint 500 in the present time but may be moved within footprint 500 in the future. This may occur, for example, when a defibrillator in an ambulance vehicle is brought within LOCATION 1 510 which in this example may be a hospital. Specifically, in this example, LOCATION 1 510 may be a hospital and position 511 of LOCATION 1 may be the emergency room wing of that hospital.

With this background on the aspects of position and location of this disclosure, referring again to FIG. 4, the defibrillator 440 is seen to occupy the position 430 which is found in the location 420 which resides in the client side network 401. In an illustrative example, the location 420 is an emergency wing of a hospital and the position 430 may be a particular position within the emergency wing of the hospital where the indicated defibrillator is located when not being used. Alternatively, the location 420 may be a fleet of emergency vehicles that support an emergency wing of a hospital and the position 430 may be a particular vehicle within the fleet where the indicated defibrillator is located when not being used. The foregoing examples further illustrate that location 420 may include locations that are stationery such as the fixed space occupied by the emergency wing of the hospital. Location 420 may also include locations that are not stationery, that is to say, that are transitory. In other words, location 420 may be a moving location that may be formed by, for example, a single emergency vehicle, or by a plurality of emergency vehicles in which case the fleet of vehicles may define the location and the individual vehicles within the fleet may define positions within that location. In yet another example, the location may be a combination of fixed and moving locations such as the combination of the emergency wing of the hospital and the fleet of emergency vehicles servicing that hospital in the previous example. Other examples of the form and shape that may be taken by both locations and positions within the scope of this disclosure will be known to one skilled in the art in view of this disclosure.

Defibrillator 440, and its various components, can be as already described with reference to FIG. 3 above. Defibrillator 440 includes a communication module 442 (390 in FIG. 3) which operates in a like manner to communication module 390 described in FIG. 3. In addition, defibrillator 440 includes a client 444 which is a program stored in a memory (338 in FIG. 3) containing instructions for execution by a processor (330 in FIG. 3) or other processors that can be used by defibrillator to illustratively provide the server with the signature data used by the server as described in this disclosure.

Both client side network 401 and host side network are part of a larger telecommunications network which is a collection of terminals, links, and nodes which connect to enable telecommunication between users of the terminals. In addition, the larger telecommunications network that the client side network and the host side network form enable telecommunication between users of the terminals in the client side network and the users of the terminals in the host side network and vice versa.

In the example of FIG. 4, only one defibrillator 440 is shown occupying a single position in a single location. However, it will be appreciated that the client side network may include a plurality of defibrillators occupying different positions in location 430. In addition, the client side network may include a plurality of locations and one or more defibrillators may occupy positions within those locations as illustrated in FIG. 5. Still referring to FIG. 4, each defibrillator in the client side network 401 has a unique address so messages or connections can be routed to and from the correct defibrillator through the network. Similarly, in the example of FIG. 4, only one server 460, database 470, and stakeholder(s) are shown. However, it will be appreciated that the network side network 490 may include a plurality of servers, databases, and/or stakeholders, and each may also have a unique address on the host side network so messages or connections can be routed to and from the plurality of servers, databases, and/or stakeholders through the network.

The links that are formed within the network that are formed by each of the client side network and the host side network connect the nodes in the network together and are built upon a transmission network which physically pushes a message across the link using circuit switched, message switched, packet switched or other routing.

FIG. 4 shows a single client side network 401 and a single host side network 490. It will be appreciated that a plurality of client side networks may be used with this disclosure as can a plurality of host side networks. For example, the network for an ambulance vehicle service may include a single host side network including a single server, a single database, and a plurality of stake holders. This single host side network may serve a plurality of client side networks illustratively with one client side network associated with one of each of a plurality of hospitals that the ambulance vehicle service may be servicing. In this way, a single host side network may track the location and movement of defibrillators residing within ambulance vehicles throughout the network of client hospitals. As another example, each hospital may also want to monitor the location and movement of ambulance vehicle defibrillators within their building. Hence, each hospital in the group may be assigned its own server, database, and stakeholders for this purpose so that each hospital may also have a host side network for purposes of monitoring the location and movement of defibrillators within its hospital premises. In this example, both the ambulance vehicle service and each hospital are provided with its own host side network for purposes of monitoring the location and movement of defibrillators within the ecosystem of each entity—namely, the defibrillators throughout all hospitals and emergency vehicles in the case of the ambulance vehicle service and the defibrillators throughout a specific hospital and emergency vehicles in the case of a specific hospital. Other combinations of host side networks and client side networks will be apparent to one skilled in the art in view of this disclosure.

Further, each of the client side network 401 and the host side network 490 may itself include one or more networks, or combinations of networks, such as an intranet network, an Internet network, a telephone network, a satellite network, and so on. The networks that may be included in the client side network and the host side network may include public or private networks. For example, the network for the ambulance vehicle service described above may configure the host side network as a private network behind a firewall that may include a wired local access network, a wireless local access network, or both. The client side network in the hospital may also be configured as a private network located behind a firewall and include a wired local access network, a wireless local access network, or both. The ambulance vehicles may be operating in a public network that may communicate with other public networks or through gateways with each private client side network as needed. Alternatively, the client side network and the host side network may be in direct communication with each through private wired, wireless, or other communication link without the need to employ the public network as a communication link for these communications. Other combinations of networks to form any configuration of a client side network and a host side network and communications therebetween will be appreciated by those skilled in the art from this disclosure.

The network formed by the client side network 401 and the host side network 490 of this disclosure may include one or more aspects of the above in operation as described in greater detail below.

Figure 6:
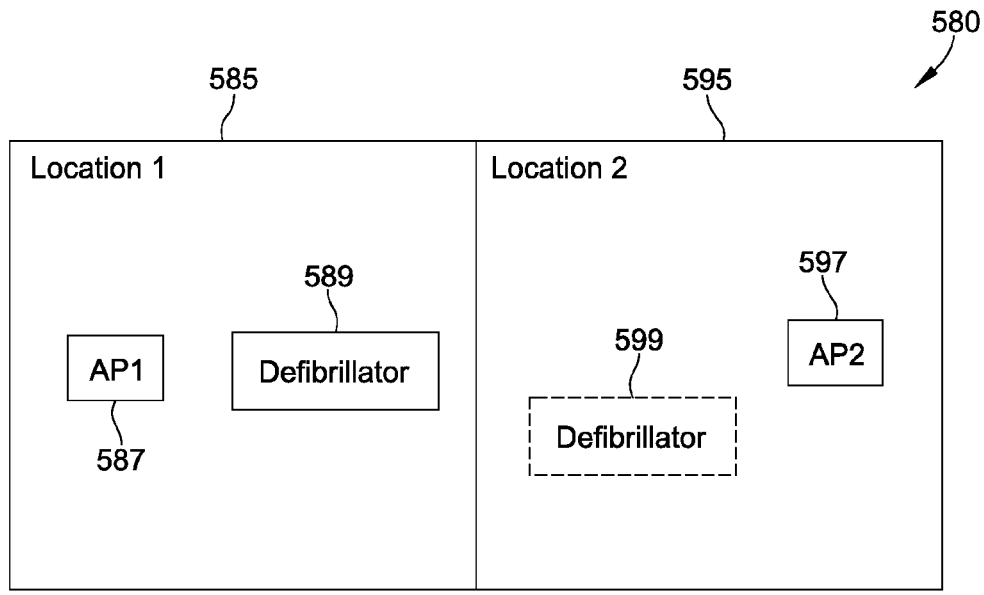
FIG. 6 shows an illustrative embodiment of the location tracking system shown in FIG. 4.

In FIG. 4, client side network 401 is illustratively shown as a wireless network comprising the TX/RX 410. The TX/RX 410 is configured for establishing a communication link 412 between the TX/RX 410 and the defibrillator 440. FIG. 6 shows an illustrative embodiment showing a TX/RX 410 configured as an access point 587 for communicating with a defibrillator 589 in Location 1 585. FIG. 6 also shows defibrillator 589 in phantom as defibrillator 599 depicting defibrillator 589 at a later point in time. Hence, defibrillator 589 in a first position within location 1 585 is seen to have moved to a second position within location 2 595 over a predetermined period of time. While in location 1, defibrillator 589 was in communication with AP1 587 and while in location 2, the same defibrillator now shown in phantom as defibrillator 599 is seen to be in communication with AP2 597. Location 1 585 and location 2 595 together may form a client side network 580, in this example, which is in communication with a host side network (490 in FIG. 4) in accordance with the teachings of this disclosure. Hence, the use of access points in specific locations enables the network to track the location and movement of the defibrillator throughout the client side network.

Figure 7:
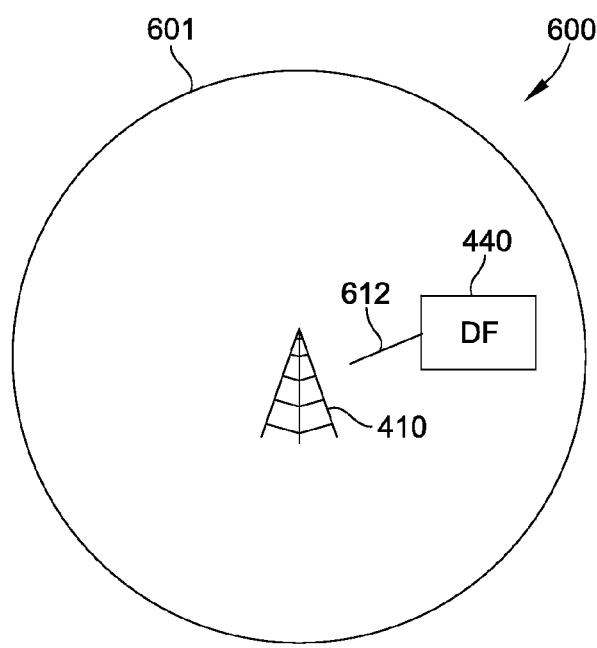
FIG. 7 shows an illustrative embodiment of another location tracking system shown in FIG. 4.

FIG. 7 shows an illustrative embodiment showing a TX/RX 410 configured as cellular base station for communicating with a defibrillator 440 residing in a cellular footprint 601 defined by the radio broadcast of the base station. In this example, the location and movement of defibrillator 440 is tracked throughout the footprint by the TX/RX 410 base station which is in communication contact with the defibrillator through a cellular communication link 612. The tracking of the movement of the defibrillator 440 by TX/RX 410 base station may be combined with movement technologies residing in the defibrillator 440 including gyroscopes, compass, altimeter, accelerometers, radio strength indicators, etc., or a combination of these movement technologies to augment/improve the location accuracy versus the wireless connection alone.

Figure 8:
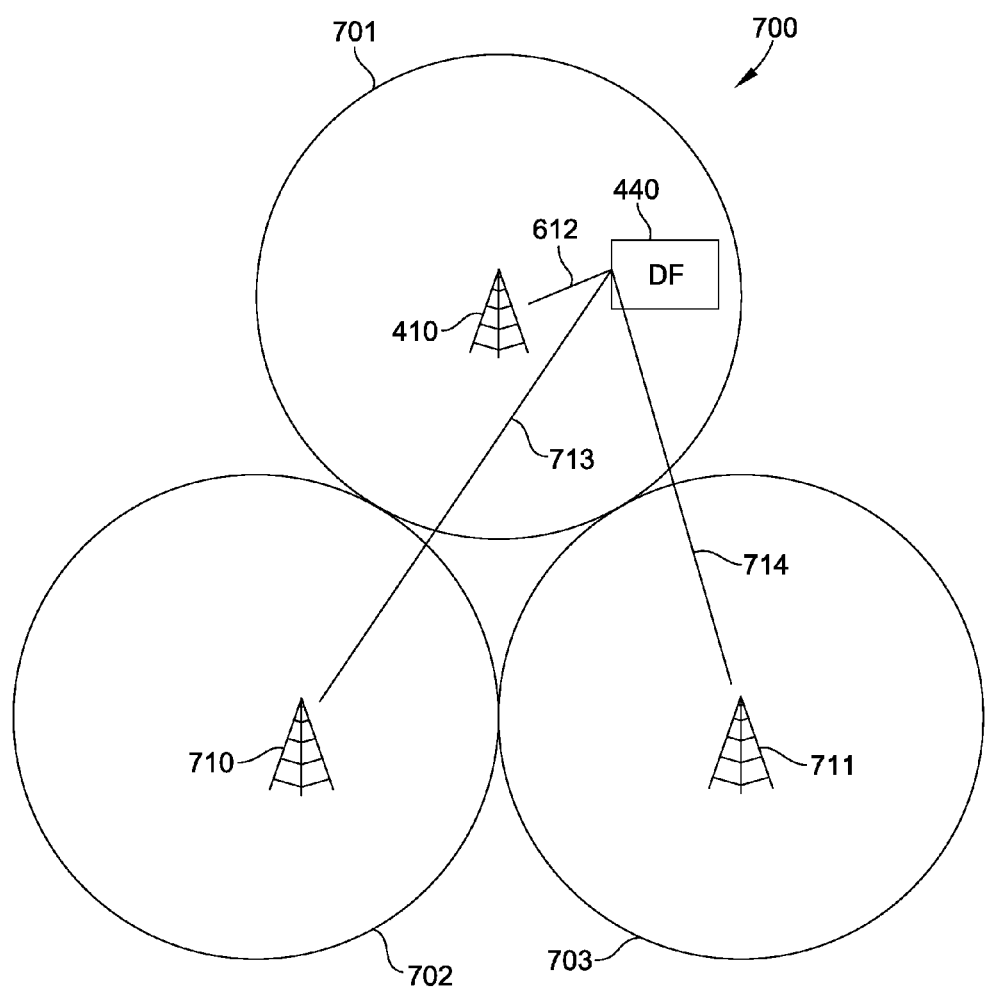
FIG. 8 shows an illustrative embodiment of another location tracking system shown in FIG. 4.

FIG. 8 shows an illustrative embodiment showing a TX/RX 410 configured as cellular base station 410 for communicating with a defibrillator 440 residing in a first cellular footprint 701 defined by the radio broadcast of the base station 410. FIG. 8 also shows a second footprint 702 defined by the radio broadcast of a base station 710 and a third footprint 703 defined by the radio broadcast of a base station 711. In this example, each of the base stations 410, 710, 711, are in communication contact with the defibrillator through communication links 612, 713, and 714, respectively. Hence, the location and movement of defibrillator 440 is tracked throughout these three footprints by at least the base stations 410, 710, and 711 in this example. The tracking of the movement of the defibrillator 440 by base stations 410, 710, 711 may be combined with movement technologies residing in the defibrillator 440 including gyroscopes, compass, altimeter, accelerometers, radio strength indicators, etc., or a combination of these movement technologies to augment/improve the location accuracy versus the wireless connection alone.

Figure 9:
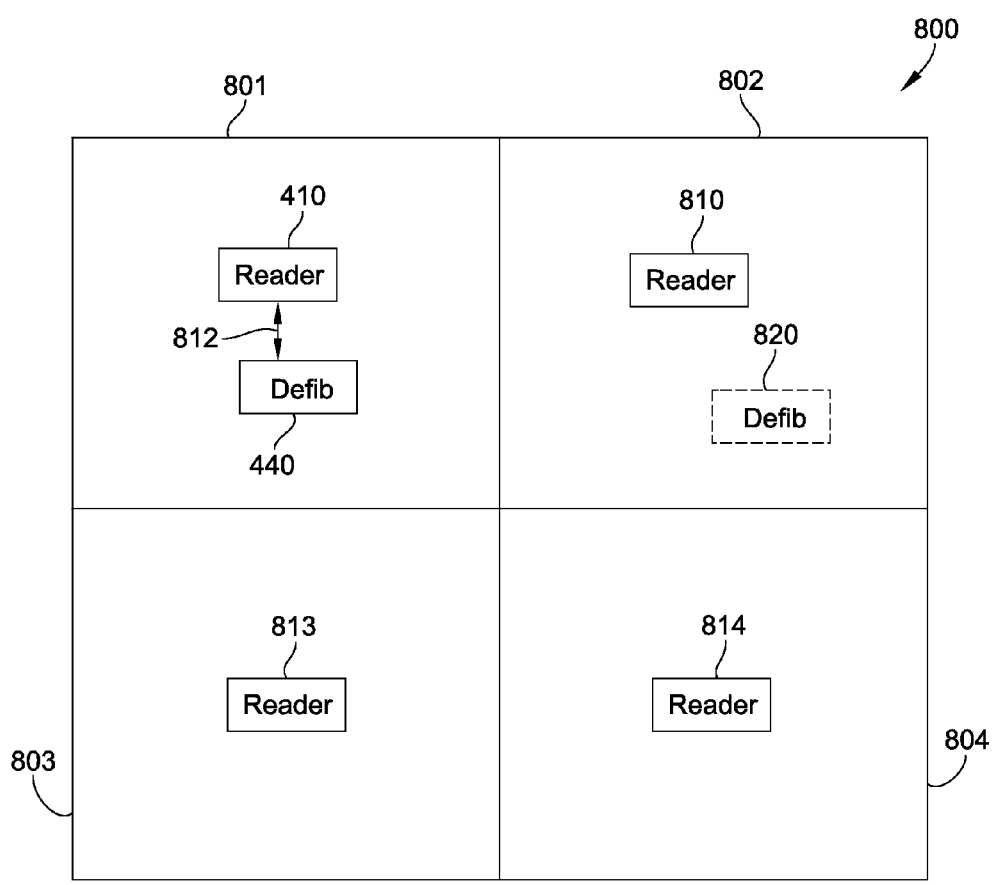
FIG. 9 shows an illustrative embodiment of another location tracking system shown in FIG. 4.

FIG. 9 shows an illustrative embodiment of a client side network 800 in which TX/RX 410 is configured as an RFID reader 410 configured for communicating with a defibrillator 440 residing in an RF footprint 801 defined by the RF broadcast of the RFID reader 410. FIG. 9 also shows a second RF footprint 802 defined by the RF broadcast of a reader 810, a third RF footprint 803 defined by the RF broadcast of an RFID reader 813, and a fourth RF footprint 804 defined by the RF broadcast of a fourth RFID reader 814. In this example, RFID reader 410 is in RF communication with defibrillator 440 through RF communication link 812. At a later point in time, defibrillator 440 will be seen to have moved into the second RF footprint 802, where the defibrillator is shown in phantom lines as defibrillator 820, at which time RFID reader 810 will form an RF communication link with defibrillator 820 for communicating with the defibrillator. Through RF communication links formed by each of the RFID readers as the defibrillator moves through the client side network 800, the location and position of the defibrillator may be tracked through the client side network 800, which is in communication with a host side network (490 in FIG. 4) in accordance with the teachings of this disclosure. The tracking of the movement of the defibrillator 440 by RFID readers 410, 810, 813, 814 may be combined with movement technologies residing in the defibrillator 440 including gyroscopes, compass, altimeter, accelerometers, radio strength indicators, etc., or a combination of these movement technologies to augment/improve the location accuracy versus the wireless connection alone.

Figure 10:
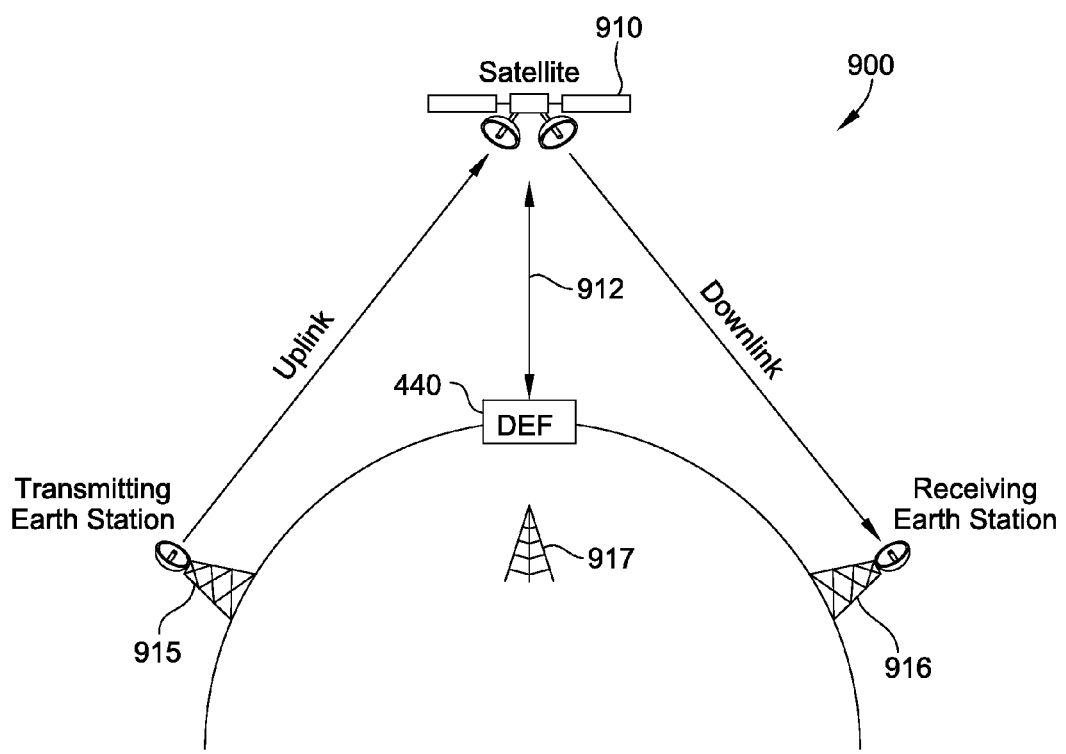
FIG. 10 shows an illustrative embodiment of another location tracking system shown in FIG. 4.

FIG. 10 shows an illustrative embodiment showing of a client side network 900 in which TX/RX 410 is configured as a satellite 910 for communicating with the defibrillator 440 over a satellite connection link 912. The satellite may be one of a plurality of satellites available for communication with devices that is visible to the defibrillator and the communication with the defibrillator may be passed on to other satellites depending on factors such as line of sight visibility and strength of signal. In this way, satellites may be used to track the location of the defibrillator throughout the client side network 900. The satellites may provide the defibrillator with GPS location data that may be used by the defibrillator according to this disclosure. In addition, the satellite 910 may be used in connection with satellite transmitting tower 915 and satellite receiving tower 916 which may enable communication between the defibrillator and the satellite through a base station 917, or a land line, that is communication with the transmitting and receiving towers 915, 916. In these and other ways, satellites alone or together with wireless, landline or other technologies may be used in accordance with this disclosure as a transmitter/receiver for tracking the location and movement of a defibrillator throughout a network. The tracking of the movement of the defibrillator 440 by satellite link 912 and/or satellite towers 915, 916 alone or together with wireless, landline or other technologies, may be combined with movement technologies residing in the defibrillator 440 including gyroscopes, compass, altimeter, accelerometers, radio strength indicators, etc., or a combination of these movement technologies to augment/improve the location accuracy versus the wireless connection alone.

In an illustrative embodiment where GPS location data from satellites is used, the defibrillator may be provided with GPS receiver and GPS circuits. The defibrillator GPS receiver detects the radio signal from the satellites and triangulates its position by getting bearing from three or more satellites. Triangulation is a geographical calculation of the distance from, and angle to, each satellite. The more satellites the defibrillator may "see," the more accurate becomes the location determination. If four or more satellites can be received, the defibrillator may also determine altitude and geographical position. The GPS coordinates generated from the satellite signals may be used by the client for determining the longitude, latitude, elevation of the defibrillator.

Referring again to FIG. 4, advantageously, the defibrillator, illustratively the client 444, is configured to generate an electronic signature for determining the position 430 of the defibrillator 440 within the location 420. Illustratively, the electronic signature comprises electronic data correlating the position 430 of the defibrillator 440 to the TX/RX 410. The electronic data correlating the position of the defibrillator to the TX/RX 410 illustratively comprises identification information on the TX/RX 410 and the strength of the signal transmitted by the TX/RX 410 to the defibrillator. The identification information on the TX/RX 410 may include the unique address of the TX/RX 410 in the client side network.

The defibrillator is configured to generate the electronic signature during a first window of time to define a first electronic signature and to generate the electronic signature during a second window of time to define a second electronic signature. According to this disclosure, each of the first electronic signal and the second electronic signal corresponds to a position. The difference between the first electronic signature and the second electronic signature corresponds to a positional state of the defibrillator.

By "positional state" is meant a condition of the defibrillator determined by correlating the current position of the defibrillator 440 with respect to a previous position occupied by the defibrillator. Referring again to FIG. 5, defibrillator DEFIB B 544 is shown to occupy the same position P2 532 at time t2 as it did at time t0. In other words, the defibrillator is seen to occupy the same position at a later point in time as it occupied at the previous point in time. The correlation between the two positions which may be determined by subtracting the later position from the first position would be zero in the case of DEFIB B 544 indicating that positional state of the defibrillator has not changed; in other words, the defibrillator 544 has not been moved. On the other hand, defibrillator DEFIB A is shown in phantom 526 to occupy a position P4 514 in LOCATION 1 510 at time t1 which is different from the position P3 513 occupied by the defibrillator 524 at time t0. The difference in distance between the two positions indicates that the positional state of the defibrillator has changed; in other words, the defibrillator has been moved. The movement of the defibrillator has occurred within the same location LOCATION 1 510 in this example.

The calculation used to calculate the difference between positions in two points in time may be based upon numerical values that may illustratively be assigned to each position by the TX/RX 410. For example, position P3 may be assigned a vector location by transmitter TX/RX 410 that is different from the vector location assigned by the TX/RX 410 to position P4 514. Alternatively, the assignment of numerical values to each position may be done in other ways as is well known to those skilled in the art Referring still to FIG. 5 defibrillator DEFIB A is shown in phantom 542 to occupy a position P3 514 in LOCATION 2 533 at time t2 which is different from the position P4 514 occupied by the defibrillator 526 at time t1. The difference in distance between the two positions indicates that the positional state of the defibrillator has changed; in other words, the defibrillator has been moved. The movement of the defibrillator has occurred from the first location LOCATION 1 510 to the second location LOCATION in this example.

Hence, if the positional state of the defibrillator indicated by the difference between the first electronic signature and the second electronic signature is other than about zero, the positional state of the defibrillator may correspond to noticeable movement of the defibrillator between a first position and a second position. In other words, the positional state indicates a condition whereby the defibrillator occupies a position in a point in time that is different from the position it previously occupied in a prior point in time since the defibrillator has been moved. The differential may indicate that the positional movement has occurred within a single location such as within a building. Alternatively, it may indicate that the positional movement has occurred between two locations. In the latter case, the positional change may signify not only that the defibrillator has been moved, but that the defibrillator has been moved between two locations such as between two buildings. In all cases, each individual electronic signature indicates the current position of the defibrillator within its location.

Referring still to FIG. 5, in order to effect the association of specific positions within specific locations, a mapping of positions to locations is generated and stored in a memory location. Illustratively, the memory storing the position-location map is stored in the server. Alternatively, the map or portions of the map may be stored in the memory residing in the defibrillator.

In either instance, the electronic signatures generated by the defibrillator during different windows of time are illustratively transmitted to the server so that the server always know the precise location of the defibrillator within the network based upon the position indicated in the electronic signature that the server receives from the defibrillator. Hence, when the defibrillator moves from a first position to a second position within the same or a different location, the server is able to detect that the defibrillator has moved and to identify the location of the defibrillator in the network after the movement.

For example, in the case of the ambulance vehicle service, a fleet of ambulance vehicles may provide a first location in the network with each ambulance in the fleet providing a specific position within that location. Although, the position of the ambulance may alone define a location within the network; one that may move within the network. Also in this example, each hospital within a group of hospitals may provide an additional location within the network and further, each hospital may define one or more positions within the hospital where a defibrillator may be permanently located. For example, one position may be a specific location in the emergency wing of a hospital. Hence, in the foregoing example, a defibrillator located in a first vehicle, that is to say, a first position within the first location defined by the fleet of ambulance vehicles may be moved from the vehicle into one of the hospitals in the example in order to continue a defibrillation procedure which began on a patient in the ambulance vehicle. The location defined by that hospital would provide a second location in this example. The locations defined by each of the other hospitals in the group would provide still other locations in this illustrated network.

This disclosure thus enables the tracking of the defibrillator from within the fleet of ambulance vehicles and specifically from within the indicated ambulance vehicle to and within the first hospital since the host side network will detect the change in position of the defibrillator from the position it occupied in the vehicle to the position it occupies in the hospital after movement of the defibrillator with the patient from the ambulance to the emergency wing of the hospital on account of the electronic signatures that the defibrillator has been transmitting to the server in the host side network throughout this process in this example. In this example, the host side network detected that the defibrillator has not only been moved; but that the defibrillator has moved to a new location—namely, the location of the first hospital from the location of the ambulance vehicle. The disclosed system may also track the defibrillator throughout the other locations defined by the other hospitals in this network throughout the time that the defibrillator may be used throughout this network of hospitals.

Figure 11:
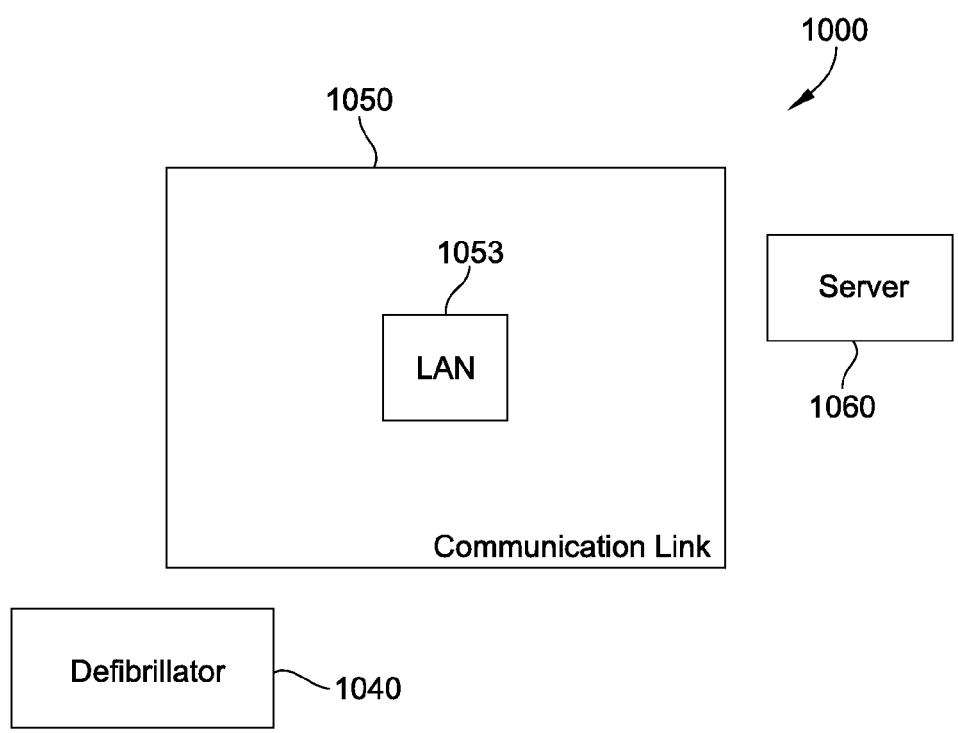
FIG. 11 shows an illustrative embodiment of a communication link aspect of the location tracking system shown in FIG. 4.
Figure 12:
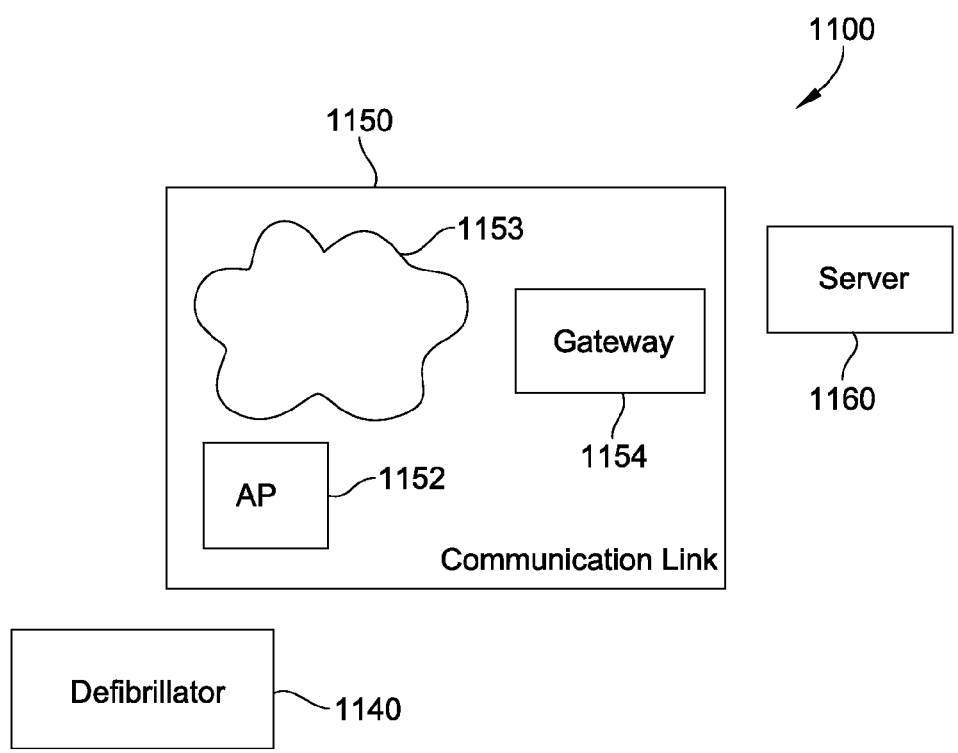
FIG. 12 shows an illustrative embodiment of an alternative communication link aspect of the location tracking system shown in FIG. 4.

Referring again to FIG. 4, communication link 450 is a communication link between the defibrillator 440 and the server 460. Communication link 450 may be an electrical communication connection between client side network 401 and host side network 490. The electrical connection may be a wireless, infra-red connection, and so on and may be configured in a local or public arrangement. For example, FIG. 11 shows a network 1000 in which a defibrillator 1040 may be connected to the server be a wireless, infra-red, etc., communication link associated with a local access network 1053 in a local access network system 1000. Illustratively, the LAN may be in one or more buildings in which the defibrillator and the server may be located. In this example, the defibrillator would need to be electrically connected wirelessly to the LAN in order for the defibrillator to communicate with the server over the communication link according to this disclosure. Alternatively, as shown in FIG. 12, the defibrillator 1140 in the client side network may be in communication with the server in the host side network wirelessly through the Internet, such as through a wireless access point 1152 that connects through a cloud 1153 to a gateway 1154 which is in communication with server 1160. The server 1160 may reside behind a firewall in a private wired local access network on which the server may be connected. In other examples, the communication link may be one or more connections through a public, a private, a combination of public and private or other network as described herein.

Communication link 450 may be an electrical connection between the defibrillator and the host side network that is configured using an electrical connection that is different in kind from the electrical connection that is established between the defibrillator and the client side network for use by the defibrillator to generate its electronic signature. For example, communication link 450 in FIG. 4 may be a WiFi access point in a building and communication link 412 may be a cellular communication link established by a TX/RX 410 configured as a base station as described in FIGS. 7, 8. Alternatively, communication link 450 may be configured to use the same connection that is established between TX/RX 410 and the defibrillator that is used by the defibrillator 430 to generate its electronic signature. For example, a WiFi access point may be configured for use by the defibrillator to generate the electronic signature as well as to communicate with the host side network.

Still referring to FIG. 4, server 460 may be any computer configured to serve the requests of the client 444 which includes a client electronic signature program running on the one or more defibrillators on a network. This computer is configured to serve the purpose of the client programs and is known as the host computer. The electronic signature programs running on the one or more defibrillators that are served by the server are a part of the client that resides on the defibrillators as discussed in this disclosure. The electronic signature client may perform some or all of the processing requests which it provides the server to maintain. The defibrillator may be provided with a graphical user interface which allows manual entry or manipulation of electronic signature and other data for tracking and location purposes. The graphical user interface also allows automated display of electronic signature and other data for tracking and location and other purposes Depending on the computing service that server 460 is configured to offer, server 460 may also include one or more of a file server for storing and making files accessible for reading and writing to the client, a print server that manages one or more printers, a network server that manages network traffic, a mail server that manages mail on a network, a database server that allows clients to interact with a database, and/or a hospital server for managing hospital records. Illustratively, server 460 may also be in communication with one or more other servers that themselves may include one or more of the foregoing or other servers.

Illustratively, the server is configured to provide information to the stakeholders 480 on the location and movement of a defibrillator or plurality of defibrillators in the network. Illustratively, this information may be stored in the database as described below and recalled by the server as needed. The server may be configured to transmit this information to the stakeholders on a scheduled or other basis. The server may also be configured to allow any stakeholder to request information on the location and movement of any defibrillator in the network. The information may be accessible by the stakeholder based upon network authorizations and preferences. The information may be accessible manually by the stakeholder or automatically by a client or other program residing in the device of the stakeholder. The information may also be accessed by the client residing in the defibrillator; in which case the defibrillator would also be acting as a stakeholder in this illustrative example. In this way, information on the location and movement of any defibrillator in the network may be made available to any stakeholder anywhere, anytime.

Illustratively, server 460 is in electrical communication with the database 470 over a wired, wireless, infrared, or other electrical link 462. Database 470 shown in greater detail in FIG. 13 includes a collection of data stored in memory. The collection of data may be aggregated and correlated as described in this disclosure. Illustratively, database 1220 comprises a first row 1230 of memory locations for storing data associated with a first defibrillator identified in the database as DEF1 1232; a series of subsequent rows 1240 of memory locations subsequent to the first row 1230 for storing data associated with subsequent defibrillators whose identification is not shown in FIG. 13; and a last row 1250 of memory locations for storing data associated with a last defibrillator identified in the database as DEFN 1252. While the first row 1230, subsequent rows 1240, and last row 1250 are in a particular order with respect to each other in the memory location, the ordering of the memory locations with respect to each other in memory may be irrelevant as is known to one skilled in the art.

In the first row of memory locations are stored electronic signature data generated by the first defibrillator identified in the database as DEF1 1232 during a window1 1233, a window2 1234, and in subsequent windows of time through windowN 1236. In the series of subsequent rows 1240 of memory locations are stored electronic signature data generated by subsequent defibrillators whose identification is not shown in FIG. 13 during subsequent windows (not shown) corresponding to a window1, a window2, and in subsequent windows of time through windowN. In the last row 1250 of memory locations are stored electronic signature data generated by a last defibrillator identified in the database as DEFN 1252 during a window1 1253, a window2 1254, and in subsequent windows of time through windowNN 1256. The database may be scaled to any number of defibrillators to record electronic signatures for each of these difibrillators during window 1N, window2, through windowNN as shown by scaling indicators 1242, 1244, 1246, 1247 and 1258 in FIG. 12. In addition, the database may be scaled to include any number of electronic signatures for each defibrillator for which data is stored in the database as illustrated by scaling indicators 1235, 1238, 1247, 1255, and 1258.

Additionally to storing the electronic signatures for each defibrillator for different windows as previously described, the database may further store the calculated differential between two electronic signatures. For example, for the defibrillator identified in the database as DEF1 1232, a differential between the electronic signature generated during window1 1233 and the electronic signature generated during window2 1234 may be calculated and stored in the database as DIF Win2-1 1237. Calculated differentials between other electronic signatures for the defibrillator identified in the database as DEF1 1232 may also be stored in the database as illustrated by DIF WinN-(N-1) 1239. In this case the letter "N" indicates the nth window in which the nth electronic signature has been calculated and the calculated differential may be this electronic signature and the electronic signature preceding it which would have been generated in the nth-1 window in this example. The differentials between electronic signatures that the system 1200 may calculate for other defibrillators in the system 1200 may also be stored in memory as illustrated by the differential DIFF Win2-1, which represents the differential between the electronic signals transmitted by defibrillator 1252 between a first and second window.

In addition to the previously described data, the database 1220 may also store other data 1261. For example, the database may store the memory map that was previously described which correlates the positions within each location in the network to that location for purposes of tracking the location and movement of the defibrillator as herein described. The information may also include information on the make and model of the defibrillator; the registered owner; the domicile of the defibrillator; a listing of authorized users and any priorities, preferences, restrictions; the user of the defibrillator; the time and place of use; the results of the use; etc. The domicile of the defibrillator may be the place where the defibrillator should be located when the defibrillator is in its home position ready to be used by a rescuer. The database may also include information on the uses that have been made by the defibrillator, the maintenance performed on the defibrillator, equipment audits that may be made on the defibrillator, and so on. Any information may be included in the database as part of the other data 1261 according to this disclosure. In this way, database 1270 provides a registry of historical electronic signature and other associated data associated with the defibrillators that are being tracked by the server 1260 throughout the network.

Figure 13:
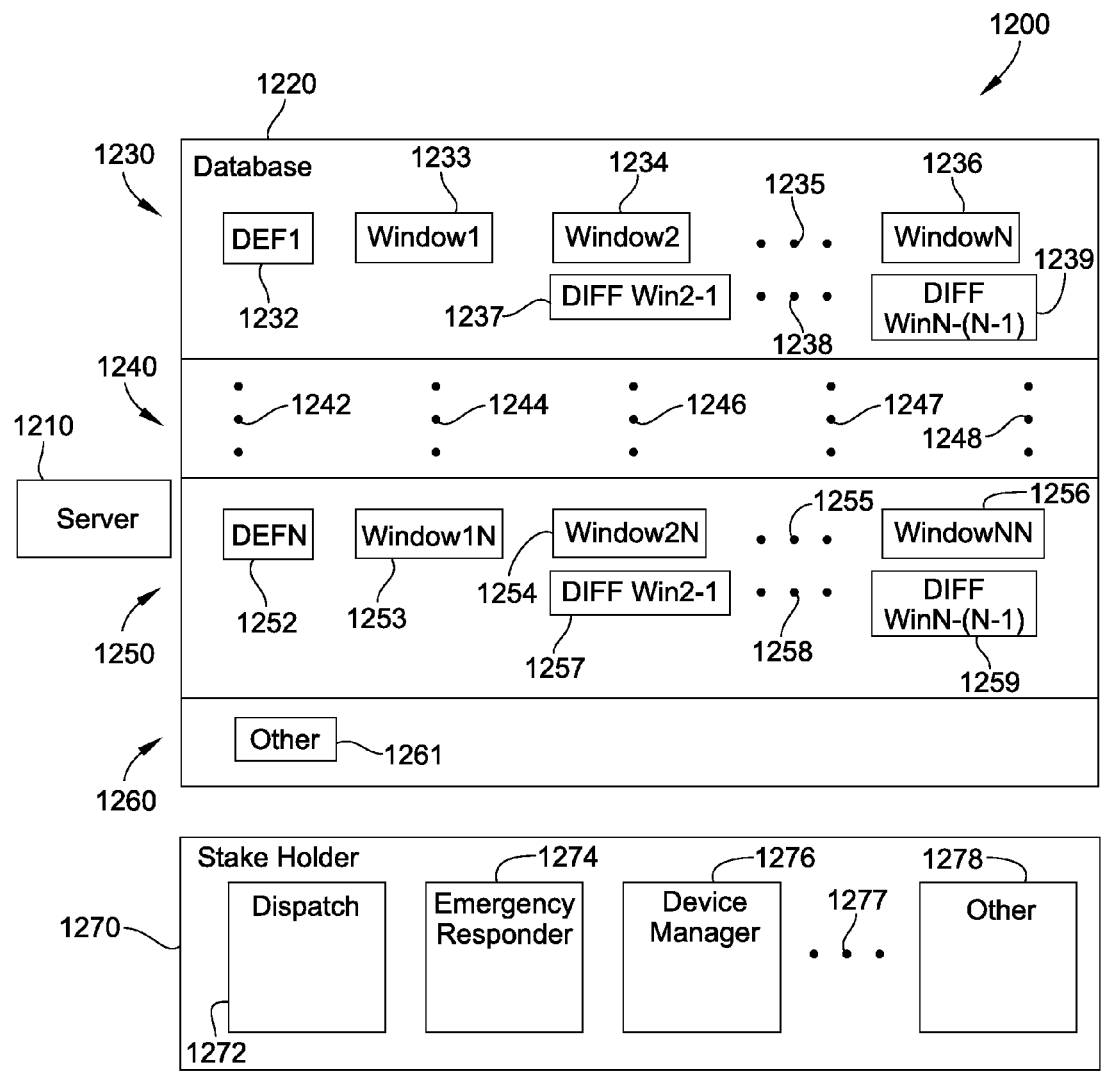
FIG. 13 shows an illustrative embodiment of the server, database and stake holder aspect of the location tracking system shown in FIG. 4.

Still referring to FIG. 13, stakeholders 1260 are illustratively terminal devices associated with one or more individuals, entities, organizations, businesses, hospitals, etc. that have a stake in tracking the location and movement of defibrillators within the network. Illustratively, the stakeholders may include a dispatch 1272, an emergency responder 1274, a device manager 1276, and others 1278 that have some interest or need to track the location and movement of defibrillators within the network. Others that may have an interest in tracking the location and movement of defibrillators within the network may be personnel responsible for maintaining equipment, or auditing the equipment for inventory management, safety or other purposes. Others that may have an interest may be a rescuer who may be in search of a defibrillator in a location and who may be able to locate a defibrillator within that location or outside that location based on this disclosure. A defibrillator too may be a stakeholder as described below. Historic data may also be useful to personnel for determining and scheduling the allocation of defibrillators across a demography based upon the uses that are being made of the defibrillators in the network according to this disclosure. This historical data may also be useful for business forecasting and planning purposes. Other uses of this historic data will be appreciated by those skilled in the art in view of this disclosure.

Referring again to FIG. 4, to operate the system for determining the positional state of a defibrillator, the defibrillator 440 is in communication with the TX/RX 410 in the client side network for the purpose of generating an electronic signature as previously described. In particular, the defibrillator is configured to generate an electronic signature for determining the position of the defibrillator within the location. The electronic signature includes electronic data correlating the position of the defibrillator to the transmitter. The electronic signature may include electronic data correlating the position of the defibrillator to the transmitter. The electronic data correlating the position of the defibrillator to the transmitter may include GPS data. The defibrillator 440 is configured to generate the electronic signature during a first window of time to define a first electronic signature and to generate the electronic signature during a second window of time to define a second electronic signature.

Illustratively, the defibrillator transmits the electronic signature generated during each window of time to the server 460 over communication link 450 for the server to calculate the differential. The communication link 450 may include TX/RX 410 or include other communication links. Alternatively, the defibrillator may itself calculate the differential between the first electronic signature and the second electronic signature corresponding to a positional state of the defibrillator and then transmit the differential to the server 450 through the network through the communication link 450. In either case, the server 460 is illustratively in communication with the defibrillator 440. In the former case, the server 460 may store each of the electronic signatures required for doing the differential calculation in the database 470. Alternatively, the server 460 may calculate the differential on the fly on receipt of a current electronic signature which may be stored in a buffer and compared to an earlier electronic signature that the server may have stored in the database 470 and retrieved from the database to make the calculation. In this example, after doing the calculation on the fly, the server 460 may store the current electronic signature in the database 470 for use in calculating a differential at a later point in time. The server may also store the calculated differential in the database 470 as previously described. The server may also alert a stakeholder on the location and movement of a defibrillator on the fly after performing the calculation. The server may also store other data pertaining to the electronic signature as previously described. In this manner, the database 470 serves as a registry of historical data on the location and movement of each of the defibrillators being tracked in the network 400.

On calculation of the differential, the server 460 may transmit the differential to a dispatch, an emergency responder, a device manager, or any other person or entity having an interest in tracking the location and movement of defibrillators. As previously described, the transmission may be scheduled by the host side network by either the server, a stakeholder, an administrator, a defibrillator, and so on. The transmission may be also be made on the fly after the server calculates the differential for example in response to an electronic signature that may have been received from a defibrillator.

The defibrillator may generate the electronic data correlating the position of the defibrillator to the transmitter based on identification information on the transmitter and the strength of the signal transmitted by the transmitter to the defibrillator. Each individual electronic signature corresponds to the current location of the defibrillator. The positional state of the defibrillator indicated by the difference between the first electronic signature and the second electronic signature may correspond to a movement of the defibrillator between a first position and a second position in the same location or between two different locations.

Figure 14:
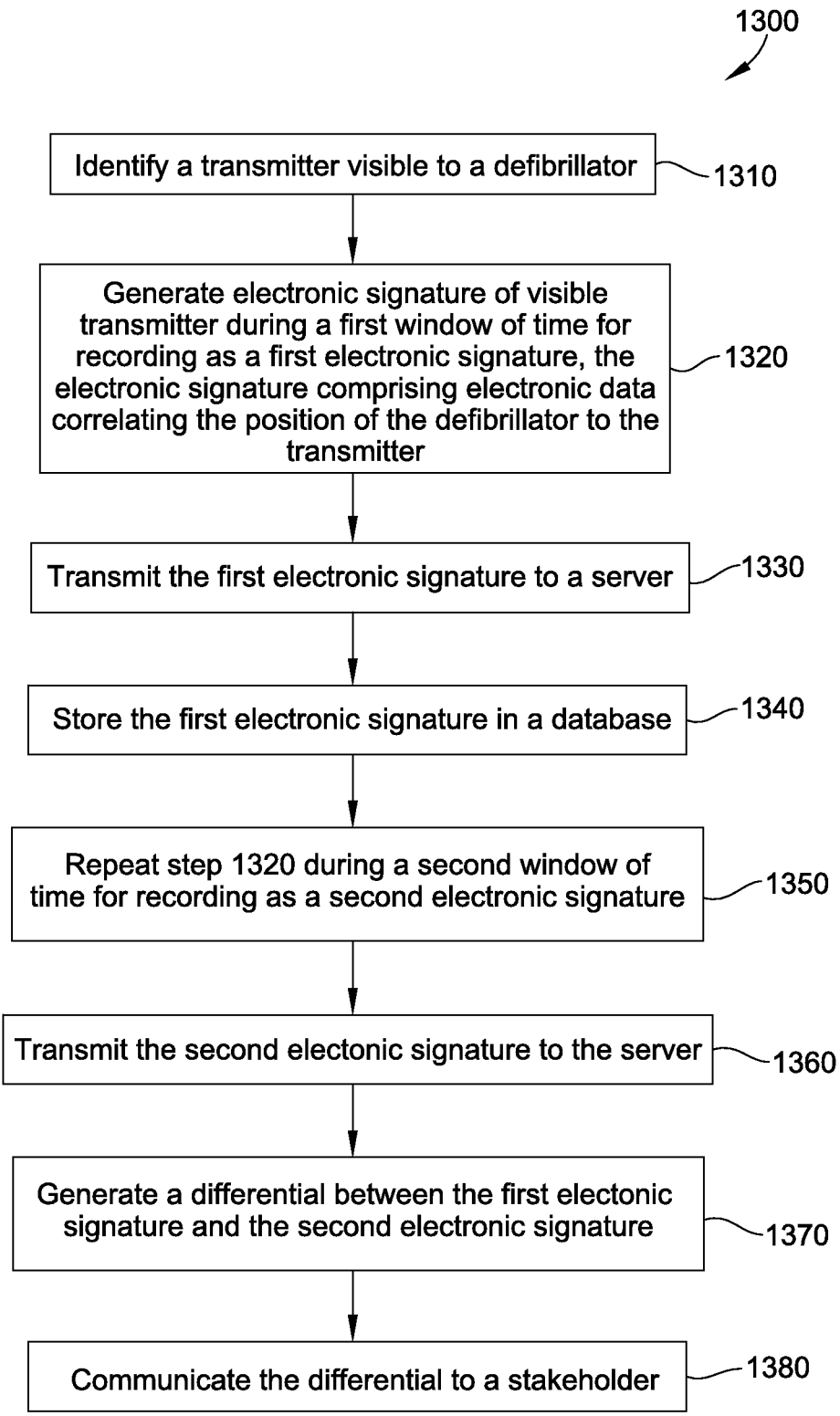
FIG. 14 is a flowchart for operating a location tracking system according to this disclosure.

FIG. 14 is a flowchart depicting one illustrative embodiment 1300 of the foregoing process for operating a location tracking system according to this disclosure. According to this flow, at step 1310, a transmitter identifies a transmitter that is visible to the defibrillator. At step 1320, the transmitter generates an electronic signature visible to the defibrillator, the electronic signature comprising electronic data correlating the position of the defibrillator to the transmitter. The electronic signature is for recording as a first electronic signature. At step 1330, the defibrillator transmits the first electronic signature to a server. At step 1340, the server stores the first electronic signature in a database. At step 1350, the transmitter repeats step 1320 during a second window of time to generate a second electronic signature. In particular, at step 1320, the transmitter generates a second electronic signature visible to the defibrillator, the electronic signature comprising electronic data correlating the position of the defibrillator to the transmitter. At step 1360, the defibrillator transmits the second electronic signature to the server. At step 1370, the server calculates the differential between the first electronic signature and the second electronic signature. At step 1380, the server communicates the differential to the stakeholder.

In alternative aspects, the server may store the second electronic signature in the database. In addition, the defibrillator may also store the first electronic signature and/or the second electronic signature in a memory residing with the defibrillator.

Figure 15:
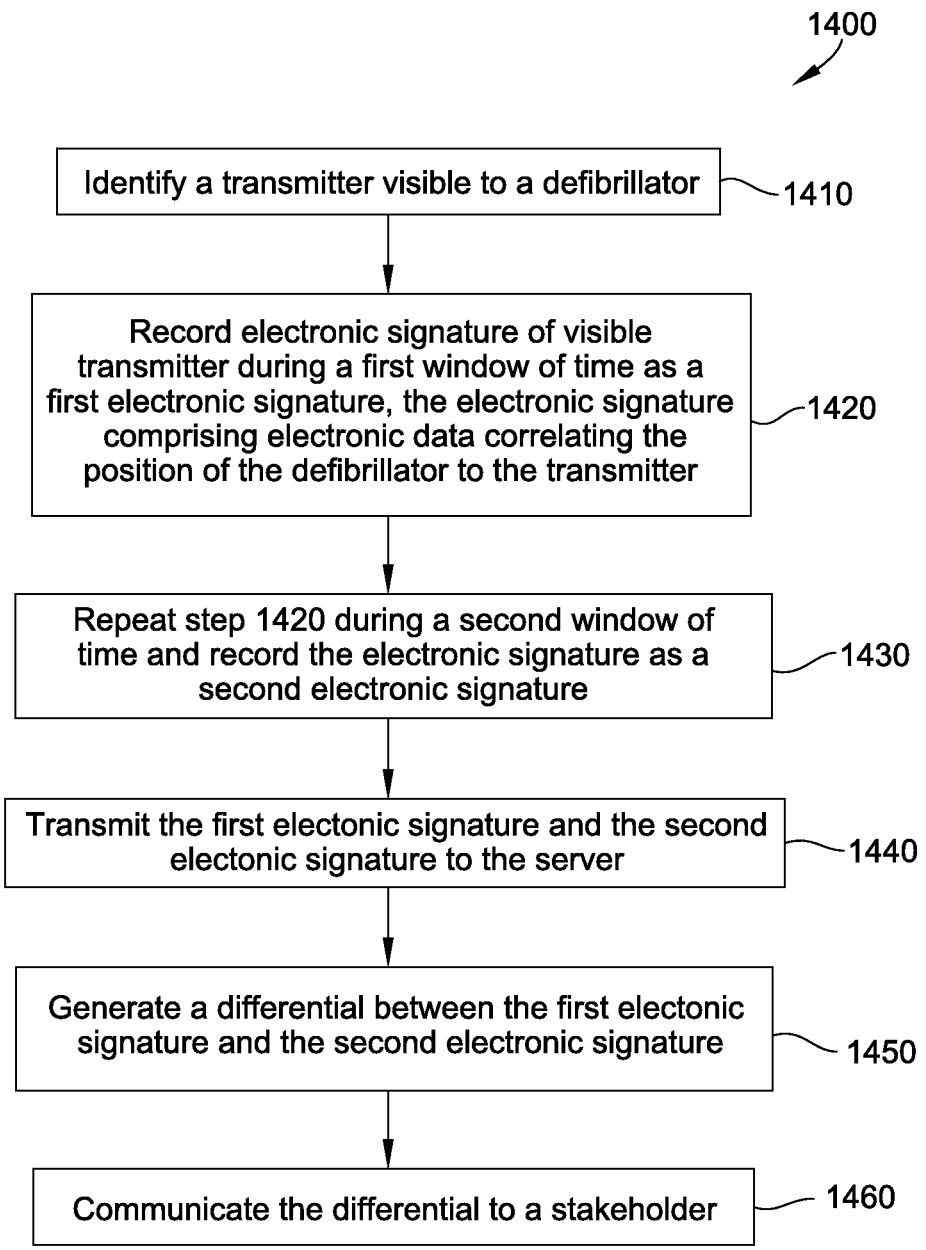
FIG. 15 is a flowchart illustrating an alternative operation for a location tracking system according to this disclosure.

A broader example of the process for operating a location tracking system 1400 according to this disclosure is shown in FIG. 15. According to this flow, at step 1410, a transmitter identifies a transmitter that is visible to the defibrillator. At step 1420, the transmitter records an electronic signature for the electronic signature visible to the defibrillator, the electronic signature comprising electronic data correlating the position of the defibrillator to the transmitter. At step 1430, the transmitter repeats step 1420 during a second window of time to record a second electronic signature. In particular, at step 1430, the transmitter records a second electronic signature visible to the defibrillator, the electronic signature comprising electronic data correlating the position of the defibrillator to the transmitter. At step 1440, the defibrillator transmits the first electronic signature and the second electronic signature to a server. At step 1450, the server calculates the differential between the first electronic signature and the second electronic signature. At step 1450, the server communicates the differential to the stakeholder. Hence, in the method 1400 of this disclosure, the defibrillator records the first electronic signature and the second electronic signature and transmits the two electronic signatures when required by a predetermined protocol. In method 1300 of this disclosure, the defibrillator feeds each electronic signature to the server when each electronic signal is generated.

Figure 16:
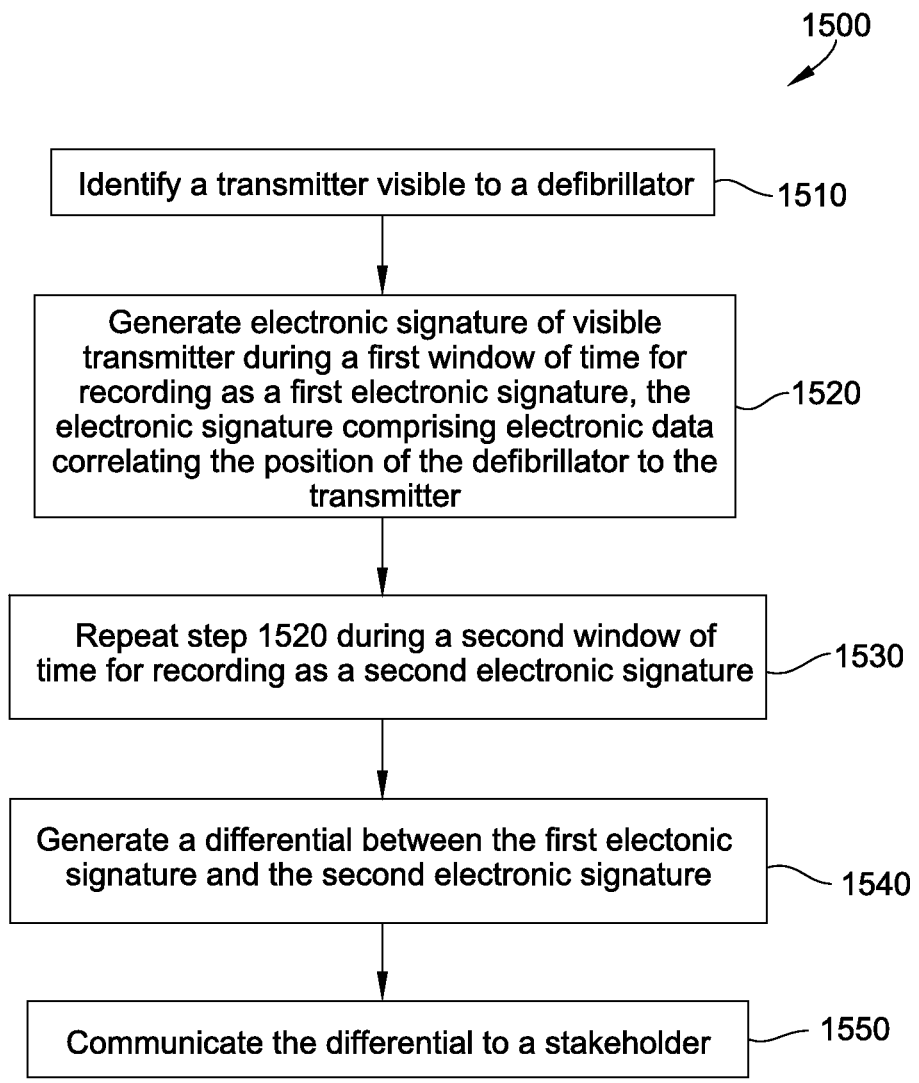
FIG. 16 is a flowchart illustrating an alternative operation for a location tracking system according to this disclosure.

An even broader example of the process for operating a location tracking system 1500 according to this disclosure is shown in FIG. 16. According to this flow, at step 1510, a transmitter that is visible to the defibrillator is identified. At step 1520, an electronic signature visible to the defibrillator during a first window of time is generated for recording as a first electronic signature, the electronic signature comprising electronic data correlating the position of the defibrillator to the transmitter. At step 1530, step 1520 is repeated during a second window of time to generate a second electronic signature for recording. In particular, at step 1530, an electronic signature visible to the defibrillator during a second window of time is generated for recording as a second electronic signature, the electronic signature comprising electronic data correlating the position of the defibrillator to the transmitter. At step 1540, the differential between the first electronic signature and the second electronic signature is calculated. At step 1550, the differential is communicated to the stakeholder. In method 1500 of this disclosure, the recording of the first and second signatures may occur by storage of the first and/or second signature in memory locations in a memory device. Alternatively, the defibrillator may retain the first and second signatures in a buffer for use in making the calculation to determine the calculated differential according to this disclosure.

In the method 1500 of this disclosure, the defibrillator records the first electronic signature and the second electronic signature, calculates the differential between the two electronic signatures and communicates the differential to the stakeholder. As previously described, the defibrillator may communicate this differential to the stakeholder through the previously described server in the host side network. Alternatively, the defibrillator may communicate the differential directly to a stakeholder. For instance, if the stakeholder is a rescuer who is in need of and trying to locate a defibrillator in a building, the rescuer may receive information on the location of a nearby defibrillator directly from the defibrillator through, for example, a network of access points as illustrated in FIG. 6. The unique address on the client side network of the device associated with the rescuer allows the defibrillator to directly ping the device of the rescuer with this information through WiFi, WAN, blue tooth or other wireless communication technology. In an alternative embodiment, the defibrillator may be programmed with information on rescuers or others authorized to be directly contacted by the defibrillator for this purpose. In this aspect of this disclosure, the information on authorized users may be kept on a server in the network and downloaded to the defibrillator on a scheduled, as needed, or other basis. For example, a host network may provide a defibrillator or defibrillators in a client side network with a set of network addresses unique to rescuers that have been dispatched to the client network to administer emergency patient care. The defibrillator may then begin pinging the unique addresses so that when the rescuers arrive, they will know exactly where they can find the defibrillators. Other ways in which the defibrillator may directly communicate location and movement position directly to a stakeholder will be known to those skilled in the art based on this disclosure.

In view of this disclosure, there is thus disclosed a defibrillator for communication with a transmitter associated with a location. The defibrillator is configured to generate an electronic signature for determining a position of the defibrillator within the location. The electronic signature includes electronic data correlating the position of the defibrillator to the transmitter. The electronic data correlating the position of the defibrillator to the transmitter may include GPS data. The defibrillator is configured to generate the electronic signature during a first and a second window of time to define a first and a second electronic signature. A differential between the first and the second electronic signatures corresponds to a positional state of the defibrillator, indicating movement within or between two locations. In a disclosed system, the first electronic signature is stored in a database and a server is configured to generate the differential and to communicate the positional state of the defibrillator to a stakeholder.

The method according to this disclosure broadly comprises the steps of: generating an electronic signature for a defibrillator for determining a position of the defibrillator within a location, the electronic signature comprising electronic data correlating the position of the defibrillator to the transmitter; generating the electronic signature during a first window of time to define a first electronic signature; generating the electronic signature during a second window of time to define a second electronic signature; determining the difference between the first electronic signature and the second electronic signature. The difference between the first electronic signature and the second electronic signature corresponds to a positional state of the defibrillator.

The method may further include the step of determining identification information on the transmitter; and determining the strength of the signal transmitted by the transmitter to the defibrillator. The positional state of the defibrillator indicated by the difference between the first electronic signature and the second electronic signature may correspond to a movement of the defibrillator between a first position and a second position. The positional state of the defibrillator indicated by the difference between the first electronic signature and the second electronic signature may correspond to a movement of the defibrillator between a first location and a second location. The positional state of the defibrillator may be transmitted to a stakeholder. The first and/or second electronic signatures may be stored in a database and retrieved for comparison to each other to determine the positional state of the defibrillator.

The client may include a graphical user interface for allowing a user to access, display, use, manipulate data on the movement and tracking of the defibrillator and to process other requests. Hence, the client may allow on-site access to historical movement and tracking data of the defibrillator by a user or one who may be in possession of the defibrillator in order to provide information to the user or possessor of the defibrillator on the home location of the defibrillator. This may also allow for on-site maintenance, calibration, auditing of the defibrillator for safety, or for other reasons as will be understood by one skilled in the art in view of this disclosure.

The defibrillator system of this disclosure provides a way for a network to track the location and movement of defibrillators by advantageously enabling defibrillators that are in communication with a network to generate electronic signatures that may be used by the defibrillator and/or network in tracking the location and/or movement of the defibrillator. The electronic signature may include electronic data correlating a position of the defibrillator to a transmitter associated with the network. The electronic data correlating the position of the defibrillator to the transmitter may include GPS data. The disclosure enables the system to use two electronic signatures generated by the defibrillator to calculate a differential position for the defibrillator. The differential position may indicate to any stakeholder that the defibrillator is in its domicile or home location or has been moved within a permitted location or outside a predetermined or permitted location.

The server of this system may be connected to any a display, a video device, an ultrasound device, a printer, a partner device either directly or through the internet to enable further use by stakeholders of the tracking information on the location and movement of defibrillators in the network. These uses may include defibrillator and/or defibrillator system management, monitoring, maintenance, auditing, business planning, forecasting or other purposes. Each of display, video device, ultrasound, printer, partner devices provide services additional to the position and location tracking information that is provided by this disclosure. For example, through this disclosure a user of an ultrasound may know the location defibrillators in the area where the ultrasound is being administered. This enables the administrator of the ultrasound to know where to locate a defibrillator during the ultrasound procedure in the event a defibrillator is needed.

This disclosure may further provide information useful for managing a set of defibrillators in the client side network. For example, if there are more than one type of defibrillators available in an area where a rescuer is in need of a defibrillator, the user may ascertain the location of the defibrillators available for use in the area and decide on the defibrillator to use based upon the features it provides. For example, if both AED and monitor defibrillators are available for use at a particular site, a trained medical personnel may quickly search out the monitor defibrillator while the non-medically trained rescuer may quickly search out the AED defibrillator based on the location and movement information provided by these defibrillators according to this disclosure.

In another illustrative example of defibrillator management within a client side network, the situation may arise where more than one rescuer in the same general location may be in need of a defibrillator at or around the same time. In an illustrative embodiment, each rescuer may interrogate the client side network for defibrillators available for use such as by polling the network for this information. Each rescuer may then select one of the defibrillators for use based on type, proximity to the rescuer, or on some other basis. According to this aspect of the disclosure, once selected, the status of a selected defibrillator will change from available to unavailable so that any subsequent rescuer will know that the selected defibrillator is unavailable for use. This minimizes the interference that may arise from two or more rescuers reaching for the same defibrillator when more than one is available; thereby leading to enhanced management of defibrillators throughout the system. In addition, this minimizes the possibility that a rescuer whose need for the defibrillator occurred later making claim on a defibrillator that another rescuer had earlier identified for use. As previously described, there is a narrow window of time for a rescuer to begin the defibrillation process after the onset of a heart condition. This disclosure thus enables defibrillators to be used on a first come first serve basis; thereby increasing the rate of survival of those patients who happen to have a rescuer who is unable to reach the defibrillator before another rescuer because he is farther away.

Management of defibrillator uses from a host location is made possible through this disclosure. Hence, any stakeholder remote from the location of the defibrillator may monitor the location and movement of one or more defibrillators in one or more client networks for purposes of maintenance, accounting, auditing, business planning, forecasting, or other purposes. For example, through this disclosure a dispatcher may direct rescuers to the location of a defibrillator with efficiency and dispatch. These efficiencies may minimize delays in the defibrillation process and increase the survival rate of subjects requiring defibrillation. As another example, this disclosure may minimize delays that may be introduced when a rescuer at a location is in need of a defibrillator but does not know where to find a defibrillator at that location. Through this disclosure the host side network may download information to the user through cellular, WiFi, or other communication methods to help the rescuer find a defibrillator in that location. As another example, if a rescuer locates the place where a defibrillator should be located but the defibrillator is not there, this disclosure may inform the user where to find that defibrillator or another defibrillator either at that location or at another location; for example, in another part of the building or in another building.

The disclosed network may provide defibrillator movement and tracking reports and data. Any report or data transaction that is generated from or in connection with the electronic signatures created by a defibrillator may be transferred throughout the network to any stakeholder. Devices of any stakeholder may retrieve the data and stakeholders take action as described in this disclosure. The data provided by this disclosure may provide a record of the location where a defibrillator is normally stored; provide a record of the location of the defibrillator when it not at its normal location; enable access to location information by, at the very least, defibrillator number and by location name; provide an up-to-date record of the relocation of defibrillator within the physical or administrative boundaries of the organization; provide an up-to-date record of any movement of the defibrillator across the physical or administrative boundaries of the organization; provide a record of the person responsible for moving the defibrillator; provide a record or a statement of the persons responsible for authorizing defibrillator movement; provide a history of the defibrillator's previous locations, while in the organization's care.

The server may enable any reports to be generated from the data taken from the electronic signature data and transmitted as needed at any time. This information may be useful in analysis to support auditing, maintenance, safety, business planning, forecasting, etc. For example, non-real-time data transfers of electronic signature reports may be used in analysis to determine location and frequency of use. This information may also be useful as data for use in designing the deployment of defibrillators in connection with future events.

The defibrillator may use any wireless communications; movement technology, including gyroscopes, compass, altimeter, accelerometers, radio strength indicators etc.; or a combination thereof to identify when a device has been moved from its known location. The defibrillator may use radio frequency measurements to identify if it has moved from its resting location. The defibrillator may use wireless communications, dynamic location tracking, real time location tracking to locate a defibrillator with this disclosure. Illustratively, the tracking of the movement of the defibrillator by wireless communications may be combined with movement technologies residing in the defibrillator including gyroscopes, compass, altimeter, accelerometers, radio strength indicators, etc., or a combination of these movement technologies to augment/improve the location accuracy versus the wireless connection alone.

Other ways to identify if a device has moved may include a customer/stakeholder activated alert. For example, if someone sees that the defibrillator is no longer where it should be, they can alert the system to locate the defibrillator. Other ways to identify a defibrillator's location may include the use of GPS, RFID. They may also include a user activated audible alert. For example, if a defibrillator is missing and the system is alerted to locate the defibrillator, the system may instruct the defibrillator to issue a visual or audible alert; thereby prompting people visible to or within earshot of the defibrillator that the defibrillator is not where it should be so that it may be returned. As another example, any person who happens upon a misplaced defibrillator may alert the system of the location of the defibrillator manually such as by pushing a button on the user interface of the defibrillator designed for the purpose or providing network alerts from a defibrillator. Hence, the defibrillator may be configured to trigger a signal for use by the system in locating the defibrillator; the signal may be triggered by activation of a manual switch residing on the defibrillator or automatically by the defibrillator directly or by the network server indirectly through the defibrillator after a predetermined period of time; and the triggered signal may activate an audible or visual alert or other alert at the site of the defibrillator or elsewhere within the network, such as at the site of the network server monitoring the defibrillator. Through this disclosure, stakeholders are educated with defibrillator movement and tracking data that allows for effective defibrillator use, deployment, planning, accounting, auditing, maintenance, historical studies, and other purposes.

In this description, numerous details have been set forth in order to provide a thorough understanding. In other instances, well-known features have not been described in detail in order to not obscure unnecessarily the description.

A person skilled in the art will be able to practice the present invention in view of this description, which is to be taken as a whole. The specific embodiments as disclosed and illustrated herein are not to be considered in a limiting sense. Indeed, it should be readily apparent to those skilled in the art that what is described herein may be modified in numerous ways. Such ways can include equivalents to what is described herein. In addition, the invention may be practiced in combination with other systems. The following claims define certain combinations and subcombinations of elements, features, steps, and/or functions, which are regarded as novel and non-obvious. Additional claims for other combinations and subcombinations may be presented in this or a related document.

We claim:

1. A defibrillator configured for two-way communication with one or more transmitter/receivers associated with a location:

the defibrillator comprising a communication module configured for two-way communication with the transmitter/receiver;

the defibrillator configured to generate an electronic signature for determining a position of the defibrillator within the location, the electronic signature comprising data correlating the position of the defibrillator to the transmitter/receiver, and the defibrillator configured to generate the electronic signature during a first window of time to define a first electronic signature and to generate the electronic signature during a second window of time to define a second electronic signature, a difference between the first electronic signature and the second electronic signature corresponding to a positional state of the defibrillator.

2. The defibrillator of claim 1 wherein the electronic data correlating the position of the defibrillator to the transmitter/receiver comprises identification information of the transmitter/receiver and the strength of the signal transmitted by the transmitter to the defibrillator.

3. The defibrillator of claim 2 wherein the identification information on the transmitter/receiver includes the electronic communication address of the transmitter/receiver.

4. The defibrillator of claim 1 wherein the positional state of the defibrillator indicated by the difference between the first electronic signature and the second electronic signature corresponds to a movement of the defibrillator between a first position and a second position.

5. The defibrillator of claim 1 wherein the positional state of the defibrillator indicated by the difference between the first electronic signature and the second electronic signature corresponds to a movement of the defibrillator between a first location and a second location, or between a first position and a second position.

6. The defibrillator of claim 1 wherein the first electronic signature further comprises data indicative of a latitude and a longitude of the defibrillator during the first window and the second electronic signature comprises data indicative of a latitude and a longitude during the second window.

7. The defibrillator of claim 1 wherein the positional state of the defibrillator indicated by the difference between the first electronic signature and the second electronic signature equal to about zero corresponds to no noticeable movement of the defibrillator from a first location to a second location.

8. The defibrillator of claim 1 further comprising one or more movement technologies residing in the defibrillator to augment/improve the location accuracy of the positional state of the defibrillator.

9. The defibrillator of claim 8 wherein the movement technology is taken from the class of movement technologies consisting of gyroscopes, compass, altimeter, accelerometers, and radio strength indicators.

10. A system for determining the positional state of a defibrillator comprising:
a transmitter/receiver associated with a location;
a defibrillator configured for two-way communication with the transmitter/receiver:
the defibrillator configured to generate an electronic signature for determining a position of the defibrillator within the location, the electronic signature comprising electronic data correlating the position of the defibrillator to the transmitter/receiver,
the defibrillator configured to generate the electronic signature during a first window of time to define a first electronic signature and to generate the electronic signature during a second window of time to define a second electronic signature
a difference between the first electronic signature and the second electronic signature corresponding to a positional state of the defibrillator; and a server configured for communication with the transmitter/receiver, the server configured to determine the difference between the first electronic signature and the second electronic signature and the positional state of the defibrillator.

11. The system of claim 10 wherein the electronic data correlating the position of the defibrillator to the transmitter/receiver comprises identification information of the transmitter/receiver and the strength of the signal transmitted by the transmitter/receiver to the defibrillator.

12. The system of claim 10 wherein the positional state of the defibrillator indicated by the difference between the first electronic signature and the second electronic signature corresponds to a movement of the defibrillator between a first position and a second position, or between a first location and a second location.

13. The system of claim 10 wherein the first electronic signature further comprises data indicative of a latitude and a longitude of the defibrillator during the first window and the second electronic signature comprises data indicative of a latitude and a longitude during the second window.

14. The system of claim 10 further comprising:
a database;
the server configured to store at least the first electronic signature of the defibrillator in the database, the server retrieving the first electronic signature from the database for comparison to the second electronic signature received from the defibrillator to determine the positional state of the defibrillator.

15. The system of claim 10 further comprising:
a stakeholder;
the server communicating the positional state of the defibrillator to the stakeholder.

16. The system of claim 10 wherein the transmitter/receiver is a base station.

17. The system of claim 10 wherein the transmitter/receiver is an access point.

18. The system of claim 10 wherein the transmitter/receiver is a radio frequency identification device.

19. The system of claim 10 wherein the transmitter/receiver is a satellite.

20. The system of claim 10 further comprising one or more movement technologies residing in the defibrillator to augment/improve the location accuracy of the positional state of the defibrillator.

21. The system of claim 20 wherein the movement technology is taken from the class of movement technologies consisting of gyroscopes, compass, altimeter, accelerometers, and radio strength indicators.

22. The system of claim 10 wherein the defibrillator is further configured to trigger a signal for use by the system in locating the defibrillator.

23. The system of claim 22 wherein the signal is triggered by activation of a manual switch residing on the defibrillator.

24. The system of claim 23 wherein the triggered signal activates an audible or visual alert or other alert at the site of the defibrillator or elsewhere within the network.

25. The system of claim 22 wherein the signal is triggered by the defibrillator after a predetermined period of time.

26. A method for determining the positional state of a defibrillator comprising the steps of:
generating an electronic signature for a defibrillator for determining a position of the defibrillator within a location, the electronic signature comprising electronic data correlating the position of the defibrillator to a transmitter/receiver with which the defibrillator is in two-way communication;

generating the electronic signature during a first window of time to define a first electronic signature;

generating the electronic signature during a second window of time to define a second electronic signature;

determining the difference between the first electronic signature and the second electronic signature;

a difference between the first electronic signature and the second electronic signature corresponding to a positional state of the defibrillator.

27. The method of claim 26 wherein the step of generating the electronic signature comprises the steps of:

determining identification information on the transmitter/receiver; and determining the strength of the signal transmitted by the transmitter/receiver to the defibrillator.

28. The method of claim 26 wherein the positional state of the defibrillator indicated by the difference between the first electronic signature and the second electronic signature corresponds to a movement of the defibrillator between a first position and a second position.

29. The method of claim 26 wherein the positional state of the defibrillator indicated by the difference between the first electronic signature and the second electronic signature corresponds to a movement of the defibrillator between a first location and a second location.

30. The method of claim 26 further comprising the steps of:

storing at least the first electronic signature of the defibrillator in a database;

retrieving the first electronic signature from the database for comparison to the second electronic signature received from the defibrillator to determine the positional state of the defibrillator.

31. The method of claim 26 further comprising the step of:

transmitting the positional state of the defibrillator to a stakeholder.

32. The method of claim 26 further comprising the step of augmenting/improving the location accuracy of the positional state of the defibrillator by one or more movement technologies residing in the defibrillator.

33. The method of claim 32 wherein the movement technology is taken from the class of movement technologies consisting of gyroscopes, compass, altimeter, accelerometers, and radio strength indicators.

34. A defibrillator configured for two-way communication with a transmitter/receiver associated with a location:

the defibrillator comprising a communication module configured for two-way communication with the transmitter/receiver; and the defibrillator configured to generate a first electronic signature for determining a position of the defibrillator within the location, the first electronic signature comprising electronic data correlating the position of the defibrillator to the transmitter/receiver, the electronic data correlating the position of the defibrillator to the transmitter/receiver including GPS data.

35. The defibrillator of claim 34 further comprising one or more movement technologies to generate a second electronic signal corresponding to a movement of the defibrillator between a first position and a second position.

36. The defibrillator of claim 35 wherein the movement technology is taken from the class of movement technologies consisting of gyroscopes, compass, altimeter, accelerometers, and radio strength indicators.

* * * * *